(12) United States Patent
McNair

(10) Patent No.: US 11,538,565 B1
(45) Date of Patent: *Dec. 27, 2022

(54) DECISION SUPPORT TOOL FOR MANAGING AUTOIMMUNE INFLAMMATORY DISEASE

(71) Applicant: CERNER INNOVATION, INC., Kansas City, KS (US)

(72) Inventor: Douglas S. McNair, Seattle, WA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/346,430

(22) Filed: Jun. 14, 2021

Related U.S. Application Data

(63) Continuation of application No. 16/731,601, filed on Dec. 31, 2019, now Pat. No. 11,037,664, which is a
(Continued)

(51) Int. Cl.
*G16H 10/60* (2018.01)
*G16H 10/65* (2018.01)
(Continued)

(52) U.S. Cl.
CPC ............. *G16H 10/65* (2018.01); *G06F 16/90* (2019.01); *G06F 16/955* (2019.01);
(Continued)

(58) Field of Classification Search
CPC ........ G16H 20/30; G16H 50/70; G16H 40/67; G16H 80/00; G16H 15/00; G16H 20/13;
(Continued)

(56) References Cited

U.S. PATENT DOCUMENTS 6,047,257 A  4/2000  Dewaele
6,555,320 B1  4/2003  Goronzy et al.
(Continued)

OTHER PUBLICATIONS

Ex-Parte Quayle Office Action received for U.S. Appl. No. 17/085,993, dated Jun. 18, 2021, 9 pages.
(Continued)

*Primary Examiner* — Tuyen K Vo
(74) *Attorney, Agent, or Firm* — Shook, Hardy & Bacon L.L.P.

(57) ABSTRACT

Decision support technology is provided for use with patients who may experience respiratory deterioration. A mechanism is provided to determine whether a patient is experiencing (or is likely to experience at a future time) an autoimmune inflammatory event, which may include performing a spectral analysis on a time series of nocturnal or axillary temperatures for the patient to determine a spectrum slope or intercept. The time series may be demeaned, detrended, and apodized before performing the spectral analysis. A comparison of the slope or intercept with a baseline value is used to determine an indication of the patient's likely condition or future condition regarding the autoimmune inflammatory event. Based on the comparison, an intervening action may be invoked, such as alerting a caregiver, providing a recommendation or modified treatment, or determining and recommending a tailored prescription of medicine for the patient.

20 Claims, 14 Drawing Sheets

Related U.S. Application Data continuation of application No. 16/157,013, filed on Oct. 10, 2018, now Pat. No. 10,586,617, which is a continuation-in-part of application No. 15/395,330, filed on Dec. 30, 2016, now Pat. No. 10,354,751, which is a continuation of application No. 14/841,093, filed on Aug. 31, 2015, now Pat. No. 9,633,169, which is a continuation of application No. 13/738,277, filed on Jan. 10, 2013, now Pat. No. 9,141,726.

(60) Provisional application No. 62/570,654, filed on Oct. 10, 2017, provisional application No. 61/585,102, filed on Jan. 10, 2012.

(51) Int. Cl.
  *G16H 10/40* (2018.01)
  *G16H 40/63* (2018.01)
  *G06F 21/62* (2013.01)
  *G06Q 50/22* (2018.01)
  *G06F 16/90* (2019.01)
  *G06F 16/955* (2019.01)
  *G16Z 99/00* (2019.01)

(52) U.S. Cl.
  CPC ......... *G06F 21/6245* (2013.01); *G06Q 50/22* (2013.01); *G16H 10/60* (2018.01); *G16H 40/63* (2018.01); *G16Z 99/00* (2019.02)

(58) Field of Classification Search
  CPC ........ G16H 10/65; G16H 10/60; G16H 40/63; G16H 8/00; G06F 16/955; G06F 16/90; G06F 21/6245; G16Z 99/00; G06Q 50/22
  See application file for complete search history.

(56) References Cited

U.S. PATENT DOCUMENTS

| | | | |
|---|---|---|---|
| 6,629,776 B2 | 10/2003 | Bell et al. |
| 7,213,969 B2 | 5/2007 | Russak et al. |
| 7,546,954 B2 | 6/2009 | Ehrhart et al. |
| 7,597,668 B2 | 10/2009 | Yarden |
| 7,698,269 B2 | 4/2010 | Zhou et al. |
| 7,698,347 B2 | 4/2010 | Vidya |
| 7,938,783 B2 | 5/2011 | Fraden |
| 7,992,773 B1 | 8/2011 | Rothschild |
| 3,054,177 A1 | 11/2011 | Graves et al. |
| 8,657,758 B2 | 2/2014 | Lia et al. |
| 8,663,106 B2 | 3/2014 | Stivoric et al. |
| 9,141,726 B1 | 9/2015 | Mcnair |
| 9,183,738 B1 | 11/2015 | Allen et al. |
| 9,215,570 B2 | 12/2015 | Schulz et al. |
| 9,323,893 B2 | 4/2016 | Berry et al. |
| 9,334,487 B2 | 5/2016 | Lundberg et al. |
| 9,426,615 B2 | 8/2016 | Vigier et al. |
| 9,633,169 B1 | 4/2017 | Mcnair |
| 10,354,751 B1 | 7/2019 | Mcnair |
| 10,431,336 B1 | 10/2019 | Murrish et al. |
| 10,553,320 B1 | 2/2020 | Mcnair |
| 10,566,082 B1 | 2/2020 | Mcnair |
| 10,586,617 B1 | 3/2020 | Mcnair |
| 11,037,664 B1 | 6/2021 | Mcnair |
| 2001/0049274 A1 | 12/2001 | Degraeve |
| 2002/0111830 A1 | 8/2002 | Tahan |
| 2002/0152239 A1 | 10/2002 | Bautista-lloyd et al. |
| 2002/0156654 A1 | 10/2002 | Roe et al. |
| 2002/0198487 A1 | 12/2002 | Brady et al. |
| 2003/0074328 A1 | 4/2003 | Schiff et al. |
| 2003/0182414 A1 | 9/2003 | Oneill |
| 2004/0147969 A1 | 7/2004 | Mann et al. |
| 2004/0153344 A1 | 8/2004 | Bui et al. |
| 2006/0229918 A1 | 10/2006 | Fotsch et al. |
| 2006/0255143 A1 | 11/2006 | Ehrhart |
| 2007/0043879 A1 | 2/2007 | Vidya |
| 2007/0083535 A1 | 4/2007 | Zilliacus et al. |
| 2007/0136202 A1 | 6/2007 | Noma et al. |
| 2007/0136279 A1 | 6/2007 | Zhou et al. |
| 2007/0138253 A1 | 6/2007 | Libin et al. |
| 2007/0282633 A1 | 12/2007 | Haider et al. |
| 2008/0021834 A1 | 1/2008 | Holla et al. |
| 2008/0097945 A1 | 4/2008 | Greis et al. |
| 2008/0126729 A1 | 5/2008 | Cai et al. |
| 2008/0208897 A1 | 8/2008 | Lew et al. |
| 2008/0294019 A1 | 11/2008 | Tran |
| 2009/0037224 A1 | 2/2009 | Raduchel |
| 2009/0069000 A1 | 3/2009 | Kindberg et al. |
| 2009/0069787 A1 | 3/2009 | Estes et al. |
| 2009/0222353 A1 | 9/2009 | Guest et al. |
| 2010/0042824 A1 | 2/2010 | Lee et al. |
| 2010/0280847 A1 | 11/2010 | Schaffer |
| 2011/0112850 A1 | 5/2011 | Beraja et al. |
| 2011/0118694 A1 | 5/2011 | Yodfat et al. |
| 2011/0276349 A1 | 11/2011 | Huang et al. |
| 2011/0295078 A1 | 12/2011 | Reid et al. |
| 2012/0041774 A1 | 2/2012 | Schmitt et al. |
| 2012/0242501 A1 | 9/2012 | Tran et al. |
| 2012/0295078 A1 | 11/2012 | Kondo et al. |
| 2013/0112557 A1 | 5/2013 | Javitt et al. |
| 2014/0062695 A1 | 3/2014 | Rosen et al. |
| 2014/0243700 A1 | 8/2014 | Pompei et al. |
| 2014/0362890 A1 | 12/2014 | Qian |
| 2015/0168154 A1 | 6/2015 | Boerger |
| 2016/0092943 A1 | 3/2016 | Vigier et al. |
| 2016/0092966 A1 | 3/2016 | Vigier et al. |
| 2016/0094946 A1 | 3/2016 | Keithley |
| 2016/0183794 A1 | 6/2016 | Gannon et al. |
| 2016/0210429 A1 | 7/2016 | Ortiz et al. |
| 2017/0169170 A1 | 6/2017 | Otin |
| 2017/0188327 A1 | 6/2017 | Shvodian |
| 2018/0295466 A1 | 10/2018 | Cannell et al. |

OTHER PUBLICATIONS

Notice of Allowance received for U.S. Appl. No. 16/913,290, dated Jun. 10, 2021, 9 pages.

Non-Final Office Action received for U.S. Appl. No. 17/560,675, dated Sep. 21, 2022, 8 pages.

```
################################################################################

#   Decision Support Tool using spectral analysis of sleeping axillary time series in rheumatoid arthritis (RA)
#   patients vs. age-gender-matched healthy controls

########################################################################## library(psd)
library(multcomp)

# initializations
filpref <- "c:/0_cerdsm/IP/temp_circadian/data/"
filsuff <- c("01","02","03","04","05","06","07","08","09","10","11","12",
        "13","14","15","16","17","18","19","20","21","22","23","24")
pref <- c("n","p")
postfix <- ".csv"

# arrays to contain illustrative cases (negative for RA; positive for RA)
neg <- rep(0,10000)
pos <- rep(0,10000)

# assemble daily pre-cleaned, demeaned, and detrended temperature time series
#   RA-negative healthy control
prefix <- pref[1]
ndx <- 1L
for (q in 1:24) {
  infil <- paste0(filpref,prefix,filsuff[q],postfix)
  # load a telemetered nightly axillary temperature dataset
  temper <- read.csv(file=infil, header=TRUE, colClasses="numeric")
  len <- length(temper$t)
  # detrend it
  fit <- lm(temper$t ~ seq(1:len))
  temper$t <- temper$t - fit$coefficients[2]*temper$t - fit$coefficients[1]
  # demean it
  av <- mean(temper$t)
  temper$t <- temper$t - av
  # apodize it
  temper.apo <- rep(0,len+4)
  temper.apo[2] <- temper$t[1]/2
  temper.apo[len+3] <- temper$t[len]/2
  for (i in 1:len) {
    temper.apo[i+2] <- temper$t[i]
  }
  # concatenate it with other dataset series members for this patient
  for (j in 1:(len+4)) {
    neg[ndx] <- temper.apo[j]
    ndx <- ndx + 1
  }
}
```

FIG. 4A.

Continues in FIG. 4B

Continues FROM FIG. 4A

.
.

```
# RA-positive patient
prefix <- pref[2]
ndx <- 1L
for (q in 1:24) {
  infil <- paste0(filpref,prefix,filsuff[q],postfix)
  # load a telemetered nightly axillary temperature dataset
  temper <- read.csv(file=infil, header=TRUE, colClasses="numeric")
  len <- length(temper$t)
  # detrend it
  fit <- lm(temper$t ~ seq(1:len))
  temper$t <- temper$t - fit$coefficients[2]*temper$t - fit$coefficients[1]
  # demean it
  av <- mean(temper$t)
  temper$t <- temper$t - av
  # apodize it
  temper.apo <- rep(0,len+4)
  temper.apo[2] <- temper$t[1]/2
  temper.apo[len+3] <- temper$t[len]/2
  for (i in 1:len) {
    temper.apo[i+2] <- temper$t[i]
  }
  # concatenate it with other dataset series members for this patient
  for (j in 1:(len+4)) {
    pos[ndx] <- temper.apo[j]
    ndx <- ndx + 1
  }
} retain 8K arrays
neg <- neg[1:8192]
pos <- pos[1:8192]

# plot the apodized, demeaned, detrended timeseries
plot(1:8192, neg, ty='l', lwd=2, col="blue", ylim=c(-1,1))
plot(1:8192, pos, ty='l', lwd=2, col="red", ylim=c(-1,1))

# determine multi-taper power spectrum
neg.psd <- pspectrum(neg)
pos.psd <- pspectrum(pos)

# plot the power spectrum
# linear freq
plot(neg.psd, log='dB', lwd=3, col="blue", xlim=c(0.0,0.2), ylim=c(-40,10), main="")
lines(pos.psd, log='dB', lwd=3, col="red")
# log freq
neg.psd.logf <- neg.psd
neg.psd.logf$freq <- log10(neg.psd.logf$freq + 0.001)
pos.psd.logf <- pos.psd
pos.psd.logf$freq <- log10(pos.psd.logf$freq + 0.001)
plot(neg.psd.logf, log='dB', lwd=3, col="blue", ylim=c(-40,10), main="")
lines(pos.psd.logf, log='dB', lwd=3, col="red")
```

Continues in FIG. 4C

Continues FROM FIG. 4B

```
# perform regression on log-log psd between -2.0 and -1.0 log(freq)
fit.neg <- lm(10*log10(neg.psd.logf$spec[25:912]) ~ neg.psd.logf$freq[25:912])
summary(fit.neg)
# Coefficients:
#                    Estimate Std. Error t value Pr(>|t|)
# (Intercept)        -45.20771   0.08801  -513.7   <2e-16 ***
# neg.psd.logf$freq  -22.77463   0.06414  -355.1   <2e-16 ***

# Residual standard error: 0.6325 on 886 degrees of freedom
# Multiple R-squared: 0.993,    Adjusted R-squared: 0.993
F-statistic: 1.261e+05 on 1 and 886 DF,  p-value: < 2.2e-16 fit.pos <- lm(10*log10(pos.psd.logf$spec[25:912]) ~ pos.psd.logf$freq[25:912])
summary(fit.pos)
# Coefficients:
#                    Estimate Std. Error t value Pr(>|t|)
# (Intercept)        -34.5924    0.1515  -228.3   <2e-16 ***
# pos.psd.logf$freq  -20.1478    0.1104  -182.5   <2e-16 ***

# Residual standard error: 1.089 on 886 degrees of freedom
# Multiple R-squared: 0.9741,   Adjusted R-squared: 0.9741
F-statistic: 3.33e+04 on 1 and 886 DF,  p-value: < 2.2e-16 both neg and pos exhibit similar ~ 20dB per decade roll-off, consistent with Brown noise spectrum
however rheumatoid arthritis temp time series spectra are right-shifted with more energy in higher bands,
# larger regression intercept values
intercept for RA pos is about 11 dB higher than healthy control perform multiple comparisons determination of statistically significant difference between the regression
coefficients for RA case vs. healthy control
ex <- data.frame(y=rep(0,1776), x=rep(0,1776), z=gl(2, 888, labels=c("NL","RA")))
for (i in 1:888) {
  ex$y[i] <- 10*log10(neg.psd.logf$spec[i+24])
  ex$x[i] <- neg.psd.logf$freq[i+24]
}
for (i in 889:1776) {
  ex$y[i] <- 10*log10(pos.psd.logf$spec[i+24])
  ex$x[i] <- pos.psd.logf$freq[i+24]
} construct analysis of variance matrix
aov.ex <- aov(y ~ z + x, data=ex)
coef(aov.ex)

K <- rbind(c(-1, 1, -1),
           c( 1, 0,  0),
           c( 0, 0,  1))
rownames(K) <- c("RA-NL", "NL-b0", "NL-b1")
colnames(K) <- names(coef(aov.ex))
summary(glht(aov.ex, linfct=K))
#       Simultaneous Tests for General Linear Hypotheses

# Linear Hypotheses:
#           Estimate Std. Error t value Pr(>|t|)
# RA-NL == 0  74.71381   0.14245   524.5  <2e-16 ***
# NL-b0 == 0 -45.07784   0.06580  -685.1  <2e-16 ***
# NL-b1 == 0 -22.67711   0.04786  -473.8  <2e-16 ***
```

*FIG. 4C.*

PATIENT: DOE, JANE MARY
AGE: 62

CURRENT CONDITIONS
☒ HYPERTENSION, BPG2
☐ ARTIRIAL FIBRILLATION
☒ RHEUMATOID ARTHRITIS

CURRENT LEVELS 142

| | |
|---|---|
| BP | 155/95 MG |
| ATRIAL | 188 |
| BLOOD GLUCOSE | 400 MG/DL |
| TEMPERATURE | 37 (C) |
| POTASSIUM | 3.4 MEQ/L |
| HBA1C | 8.5 % |
| WEIGHT | 95 KG |
| BMI | 30 KG/M2 |
| WAIST/HIP RATIO | 0.98 |

*FIG. 5A.*

PATIENT: DOE, JANE MARY
AGE: 62

CURRENT CONDITIONS
☒ HYPERTENSION, BPG2
☐ ARTIRIAL FIBRILLATION
☒ RHEUMATOID ARTHRITIS

CURRENT LEVELS 142

| | |
|---|---|
| BP | 155/95 MG |
| ATRIAL | 188 |
| BLOOD GLUCOSE | 400 MG/DL |
| TEMP | 37 DEG (C) |
| POTASSIUM | 3.4 MEQ/L |
| HBA1C | 8.5 % |
| WEIGHT | 95 KG |
| BMI | 30 KG/M2 |
| WAIST/HIP RATIO | 0.98 |

*FIG. 5B.*

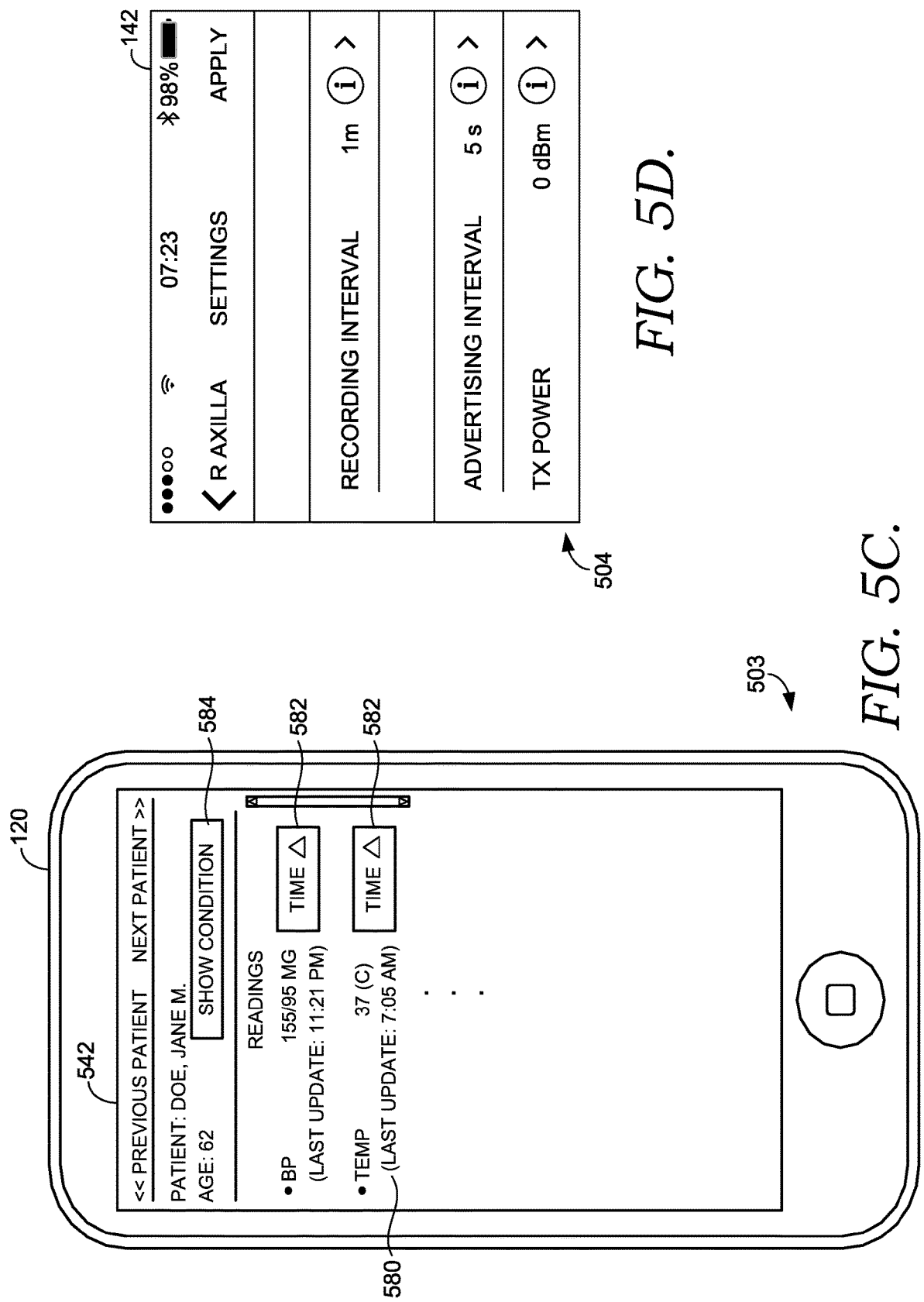

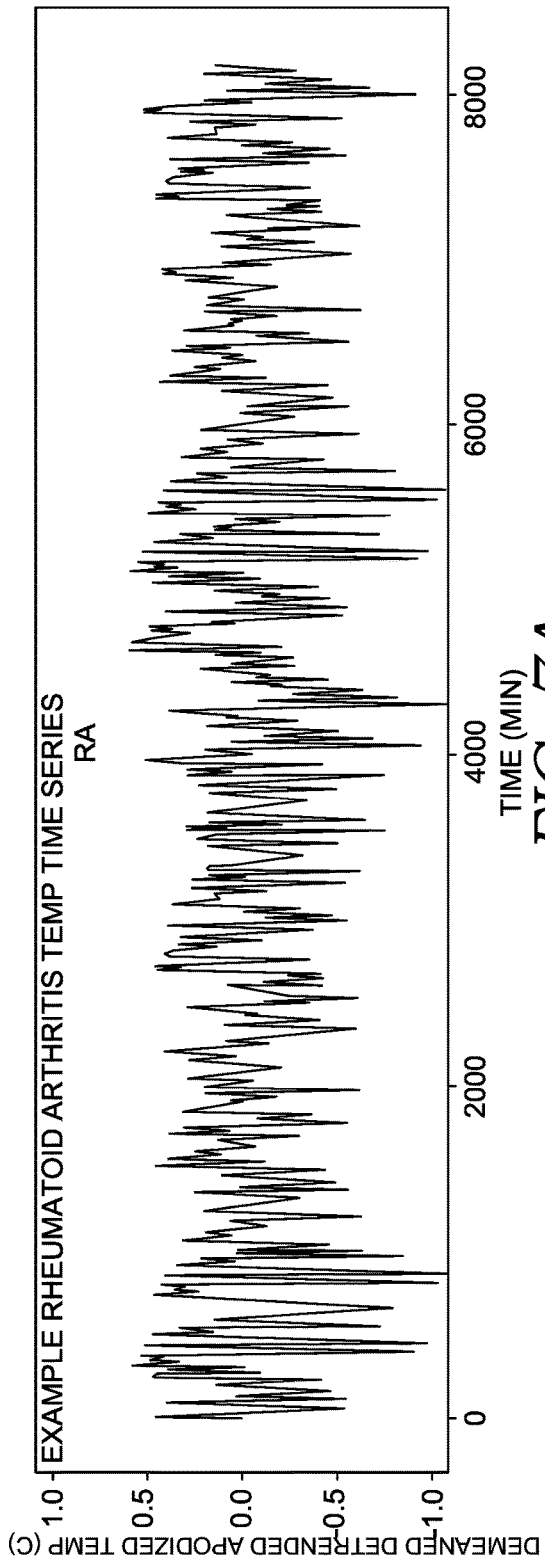
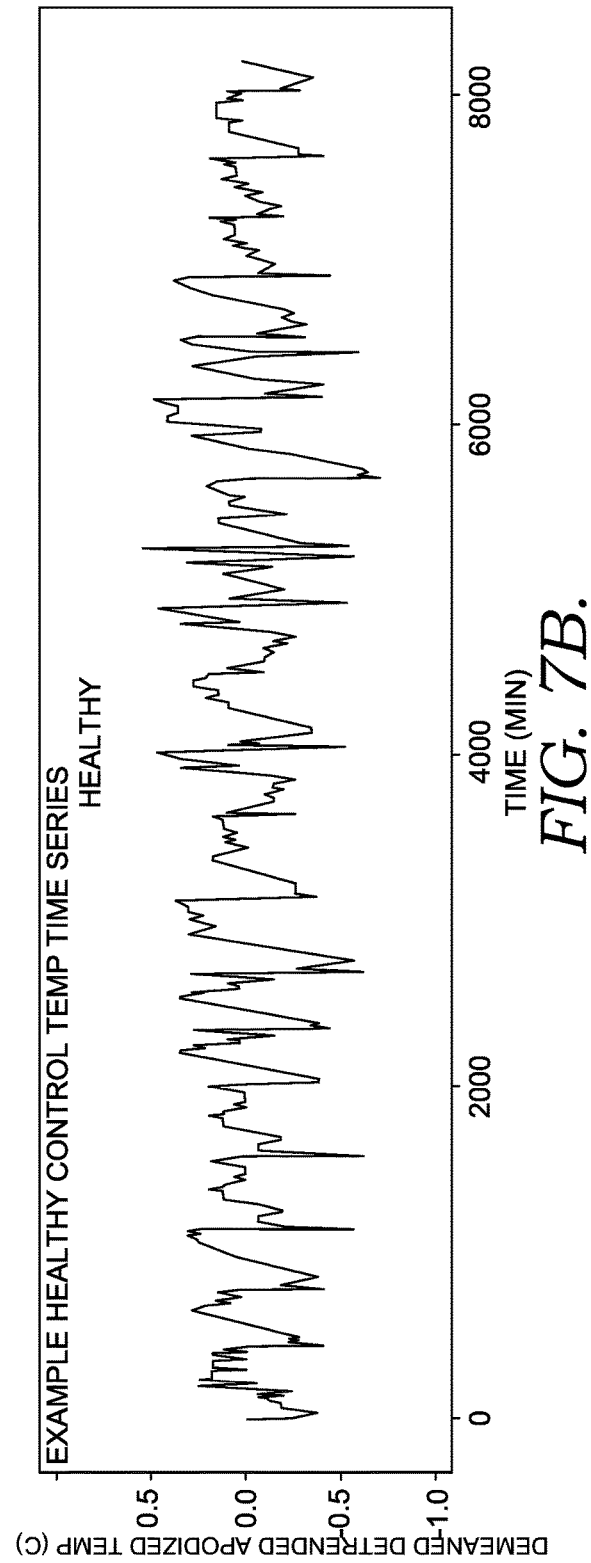

DECISION SUPPORT TOOL FOR MANAGING AUTOIMMUNE INFLAMMATORY DISEASE

CROSS-REFERENCE TO RELATED APPLICATIONS

The present application claims the benefit of U.S. Non-Provisional application Ser. No. 16/731,601, entitled "Decision Support Tool for Managing Autoimmune Inflammatory Disease," filed Dec. 31, 2019, which is claims the benefit of U.S. Non-Provisional application Ser. No. 16/157,013 (now U.S. Pat. No. 10,586,617), filed Oct. 10, 2018, which is claims the benefit of U.S. Provisional Application No. 62/570,654, filed Oct. 10, 2017, each of which is hereby expressly incorporated by reference in its entirety. The U.S. Non-Provisional application Ser. No. 16/157,013 is also a continuation in part of, and claims priority from, U.S. patent application Ser. No. 15/395,330 (now U.S. Pat. No. 10,354,751), filed Dec. 30, 2016, entitled "Computerized Systems And Methods For Providing Mobile-Device Updates Of Electronic Health Records," which is a continuation of, and claims priority from, U.S. patent application Ser. No. 14/841,093 (now U.S. Pat. No. 9,633,169), filed Aug. 31, 2015, entitled "Computerized Systems And Methods For Providing Mobile-Device Updates Of Electronic Health Records," which is a continuation of, and claims priority from, U.S. patent application Ser. No. 13/738,277 (now U.S. Pat. No. 9,141,726), filed Jan. 10, 2013, entitled "Computerized Systems And Methods For Providing Mobile-Device Updates Of Electronic Health Records," which claims the benefit of U.S. Provisional Application No. 61/585,102, titled "Computerized Systems And Methods For Providing Mobile-Device Updates Of Electronic Health Records," filed Jan. 10, 2012; each of which is hereby expressly incorporated by reference in its entirety.

BACKGROUND

The modern practice of medicine poses a number of information-related challenges for clinicians to effectively deliver quality care to patients having an autoimmune inflammatory disease, such as rheumatoid arthritis. The American Autoimmune Related Diseases Association (AARDA) estimates that approximately 50 million (16%) of people in the United States are affected by an autoimmune disease, while NIH more conservatively estimates that autoimmune diseases collectively affect approximately 24 million (7%). Autoimmune inflammatory diseases include rheumatoid arthritis, systemic lupus erythematosus ('lupus'), Crohn's disease and ulcerative colitis (or other inflammatory bowel disease), psoriasis, multiple sclerosis, scleroderma, celiac disease, Graves' disease, and Type 1 diabetes mellitus, or hemophagocytic lymphohistiocytosis (HLH) or its prodrome. Women are more commonly affected by autoimmune diseases than men. Often the autoimmune disease starts relatively early in life.

Currently, autoimmune disease-related healthcare expenses exceed $100 billion per year in the U.S. By comparison, cancer costs total approximately $57 billion annually. Autoimmune inflammatory diseases can affect almost any part of the body, including the heart, brain, nerves, muscles, skin, eyes, joints, lungs, kidneys, endocrine and exocrine glands, the digestive tract, and blood vessels. The classic sign of an autoimmune disease is inflammation, which can cause redness, heat, pain, and swelling. How an autoimmune disease impacts the patient depends on what organ system or part of the body is most-affected. If the disease predominantly affects the joints, as in rheumatoid arthritis, the patient may experience joint pain, stiffness, and loss of function. If it predominantly affects the thyroid, as in Graves' disease and thyroiditis, it may cause tiredness, weight gain, and muscle aches. If it predominantly attacks the skin and kidneys, as it does in scleroderma and systemic lupus, it can cause rashes, blisters, skin color changes, and progressive loss of kidney function. Many autoimmune diseases do not restrict their damage to one part of the body. For example, lupus can affect the skin, nerves, joints, kidneys, heart and blood vessels. Type 1 diabetes can affect eyes, kidneys, muscles, nerves, the vascular system and heart, and more.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Improved monitoring and decision support technology is provided for human patients having a systemic autoimmune inflammatory condition or disease, such as rheumatoid arthritis, lupus, psoriasis, or Crohn's disease. In particular, a mechanism is provided to more accurately monitor the patient's condition, which may include more accurately determining a prognosis, diagnosis, a current or projected impact of the autoimmune inflammatory disease on the patient and/or whether the patient is experiencing an autoimmune inflammatory event (or is likely to experience such an event over a future time interval), and to provide decision support to the patient or caregiver associated with the patient, which may include determining or implementing an appropriate response action such as automatically issuing an alert or notification to the caregiver. A time series of nocturnal or axillary temperatures for the patient is determined and a spectrum analysis is performed on the time series to further determine a spectrum slope and intercept in a frequency passband. The nocturnal or axillary temperatures may be determined using a high-frequency measurements (e.g., 1 measurement per minute over a set of nightly sleeping episodes) using an RF beacon temperature sensor device worn by the patient, in some embodiments. Therefore, in some instances, embodiments further include detecting the proximity of a wearable RF beacon to a computing device, such as a smartphone or mobile computing device of the patient (or other authorized caregiver/user), via periodic RF transmissions emitted by the temperature sensor-enabled beacon device of the beacon-bearing patient. In some instances, the time series may be preprocessed, which may include trimming, cleaning, demeaning, detrending, and apodizing the temperature time series before performing the spectral analysis to determine spectrum slope and intercept frequency passband.

Next, a comparison may be performed on the current or recent spectrum slope and intercept vs. a normal or baseline values for a reference patient or from the patient's own previous values. Based on the comparison, one or more actions may be carried out automatically or may be recommended, such as, without limitation, intervening in the patient's care; modifying a care program for treating the patient; automatically scheduling interventions or consultations with specialist caregivers; or generating notifications such as electronic messages, which may include recommendations; information, such as electronically presenting spectrum analytic interpretive information pertaining to the patient to an authorized clinician or to the patient or caregiver/user; alerts, or alarms, based on the comparison which may be emitted or otherwise provided to the caregiver and/or to the patient. Further, in some embodiments, based on the comparison, prescribed medication may be more accurately tailored to the patient's specific condition at an appropriate time, thereby personalizing medication to the patient. Some embodiments may be used for continually monitoring or tracking a clinical status of a patient in an ambulatory setting or at home.

In this way, embodiments of the technology disclosed herein may facilitate allowing in-home caregivers, physicians, nurses, and clinical case managers to provide more safe and effective care for each patient. Moreover, embodiments of the technology described herein improve upon conventional technologies for managing systemic autoimmune inflammatory conditions by establishing a means whereby altered body temperature power spectrum properties may be transformed so as to guide efficacious adjustment of a patient's medication regimen treating an autoimmune condition and to guide the chronopharmaceutical optimal tailoring and personalized timing of the administration of one or more medications comprising said regimen to accomplish improved relief from symptoms and to better retard progression of the patient's illness. It is not generally routine and conventional to determine, adjust, or administer a medication regimen based on a series of body temperatures or the altered body temperature power spectrum. Additionally, in this way, embodiments facilitate preventing abuse, over-prescription, or patient pain and suffering due to under-prescription of medication, and reduce the likelihood of occurrences of patient addiction to narcotics by enabling a more accurate and timely prescription of medications to be tailored to the patient (which may be based on their specific condition determined by the comparison) and/or by providing a verifiable medical indication (which can be recorded in the a health record or claims record) of an autoimmune inflammatory event being experienced by the patient. Thus a patient may be prescribed medication only if they need it and only in a dosage that is customized to their particular status or condition.

BRIEF DESCRIPTION OF THE DRAWINGS

The present technology is described in detail below with reference to the attached drawing figures, wherein:

FIGS. 4A-4C illustratively provide an example embodiment of a computer program routine for monitoring and determining that a patient is undergoing (or will experience at a future time interval) an autoimmune inflammatory condition event based on a power spectrum derived from a sleeping temperature time series of the patient, in accordance with an embodiment of the present disclosure;

FIGS. 5A-5D depicts aspect of an example user interfaces for monitoring a patient and/or receiving information from a RF beacon suitable for use in an embodiment of this disclosure;

FIGS. 7A-7B depict examples of concatenated time series of 24 days' nocturnal temperatures acquired during sleep at a sampling rate of 1 sample per minute, for a representative patient having rheumatoid arthritis and from a representative healthy normal person, respectively, and determined in accordance with an embodiment of this disclosure.

DETAILED DESCRIPTION

Figure 1A:
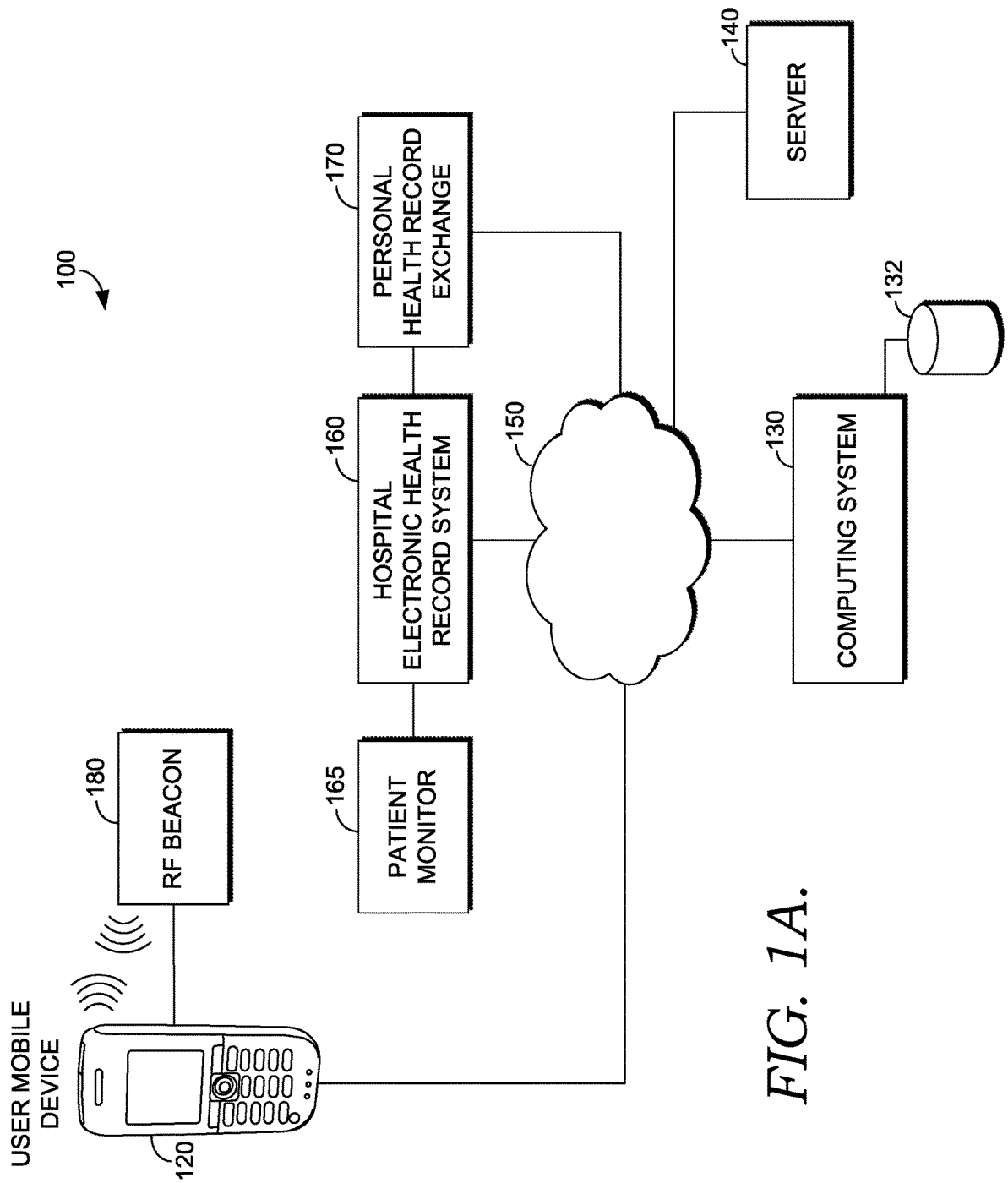
FIGS. 1A, 1B, and 1C depict aspects of an illustrative operating environment and example system architecture suitable for embodiments of the present disclosure.

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of this disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the present technology takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or non-transitory technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Aspects of the technology described herein provide improved decision support for the healthcare of patients having an autoimmune inflammatory disease. For instance, embodiments described herein may be utilized for monitoring patients (including patients at home or ambulatory settings or for telemedicine scenarios) and quantitatively determining whether or not a significant change in their status meriting medical intervention has likely materialized or is in the process of emerging. In an embodiment, a clinical decision support tool is provided that determines a likelihood, which may be expressed as a score, that the patient is experiencing or will experience an autoimmune inflammatory event or episode. The temperature information utilized for determining the score may be derived from periodic RF beacon transmissions emitted by a temperature sensor-enabled beacon device, which may be worn by the patient. Use of such a device is not generally well-understood, routine, or conventional in the field for diagnosing or predicting the likelihood of an autoimmune inflammatory event. Further, the discovery that a series of temperatures or the frequency domain of the temperature measurements enables the use of temperature-sensor beacon devices for diagnosing or predicting autoimmune inflammatory events, thereby improving the technology of these devices, as they devices are enabled for new uses. The score may include a statistical probability or prediction, which may be used by the decision support tool to determine and/or invoke a particular action in response to the score. For example, based on the generated score (or results of the spectral analysis and comparison, as described herein), one or more actions may be carried out automatically or may be recommended, such as, without limitation, intervening in the patient's care, modifying a care program for treating the patient, automatically scheduling interventions or consultations with specialist caregivers, or generating notifications such as electronic messages, which may include recommendations, information, alerts, or alarms, based on the forecast which may be emitted or otherwise provided to the caregiver and/or to the patient. For instance, in an embodiment, drugs may be more accurately prescribed to a patient based on their specific condition (which is more accurately determined via the embodiments of the technology described herein), such as the prescribing of DMARD, anti-TNF, anti-IL1, anti-IL-6Ra drugs.

In this way, embodiments of the technology prevent abuse, over-prescription, or patient pain and suffering due to under-prescription, of medication. Another improvement provided by embodiments of the technology disclosed herein is to reduce the likelihood of occurrences of patient addiction to narcotics by enabling a more accurate and timely prescription of medications to be tailored to the patient (based on their specific condition or likely future condition determined by the score) and/or by providing a verifiable medical indication (which can be recorded) of an autoimmune inflammatory event being experienced by the patient. Thus patients may only receive medication if they need it and only receive a dosage that is customized to their particular status, as indicated by the score or comparison. In some embodiments, a score or indicator or a patient's probability of experiencing an autoimmune inflammatory event currently or at a future time interval may be provided and utilized to determine recommendations regarding intervention or other changes in treatments plans. Intervening actions may also include recommendations or preventive actions that may be clinically indicated and such that the patient's adherence to effective prevention or treatment regimens yields indicia of reduced risk.

For example, some embodiments described herein entail a system that can accommodate frequent acquisition and radio transmission of temperature measurements, which maybe received from a temperature sensor-enabled beacon device, to a computing device (such as a smartphone, backend server, or other computing device) that implements a method embodiment described herein, to detect or predict an autoimmune inflammatory event. Further, other advantages and improvements of the embodiments described herein, verses conventional technologies for monitoring patients having an autoimmune inflammatory disease, include that, to date conventional wearable wireless digital thermometers utilized in health care settings have been directed to low sampling-rates or ad hoc intermittent on-demand measurement of temperature. In particular, the conventional wearable thermometers and monitoring processes are not configured for applications utilizing high sampling-rates, such as acquiring temperature measurements once per minute or greater, nor has any conventional or prior wearable thermometer and measurement process been designed to have a low thermal time-constant so as to be able to accurately reflect rapid fluctuations in the temperature of body tissues with which the thermometer is in contact. By contrast, at least some embodiments described herein are specifically directed to ascertaining the frequency power spectrum properties of body temperature time series in the frequency range between $1.0 \cdot 10^{-3}$ min-1 and $6.0 \cdot 10^{-1}$ min$^{-1}$. In some instances, this is accomplished utilizing a sensor-beacon device whose mechanical construction affords a thermal time constant or 0.3 min$^{-1}$ or less. Some embodiments also improve on conventional decision support technologies for autoimmune inflammatory diseases by overcoming certain drawbacks, such as providing a means for longitudinally calculating and tracking the patient's status and likelihood of experiencing an autoimmune inflammatory event.

Accordingly, as will be further described, systems and computerized methods are provided for monitoring the clinical and physiological status of a patient, generating an analysis, such as a score, indicating the condition of autoimmune inflammatory disease (which may be occurring or emerging, or a likelihood of a future occurrence, which may occur over a future time interval) and providing computer-performed decision support, which may include invoking one or more actions or recommendations. In some embodiments, these systems or methods are incorporated into a decision support tool used for screening, monitoring, and/or treating the patient.

In one aspect, a method embodiment comprises receiving nocturnal or ultradian core or axillary temperature information from a patient. The temperature information may be received or derived from periodic RF beacon transmissions emitted by a temperature sensor-enabled beacon device, which may be worn by the patient. In some embodiments, at least 4 hours' measurements are acquired in each nighttime sleep episode, comprising the bathyphase of the patient's diurnal temperature cycle. In some embodiments, temperatures are measured at a high sampling rate, such as at least one measurement per minute. A temperature time series may be determined from nocturnal core or axillary temperature information received from the RF beacon, which may be received over several weeks or more of nightly sleeping episodes. In some instances, preprocessing operations maybe performed on the temperature information time series. For example, the silent leaders or trailers of the time series or outlying temperature values (which may represent temperature readings acquired when the RF beacon or temperature sensor was not in contact with a patient's body and thus provided an erroneous temperature reading). Further, in some embodiments preprocessing may include detrending, demeaning, and cleaning the time series (e.g., eliminating outliers). In some embodiments, preprocessing may include apodizing the temperature time series.

A number of recent temperature time series entries are then extracted to generate a time series of recent temperature measurements. In some embodiments, the length of the time series is at least eight thousand measurements; for example in one example embodiment reduced to practice, the extracted recent temperature time series comprises 8,192 measurements. In some embodiment, a current day or nights temperature information may be appended to the time series of recent temperature measurements.

Next, the method may determine whether a sufficient number of nightly temperature measurements have been acquired or received. If not, then the method may wait for a time interval before receiving or determining additional temperature information. In some embodiments, the method may wait for the next minute to receive an additional temperature measurement or the method may wait until the next night when the patient is sleeping and in proximity to an operating temperature-sensor beacon. If, however, enough nightly temperature measurements have been received, then a spectral analysis is performed on the temperature time series to determine a spectrum slope (1/F slope) and intercept in frequency passband. Based on this determination, the method performs a comparison of the spectrum analysis results vs. baseline values, which may be established from a reference patient or population or based on the patient's own previous values. The baseline values may be determined from a spectrum analysis on temperature time series of a health control population, such as described in the example embodiment reduced to practice. For example, the baseline may be derived from patients without having an autoimmune inflammatory condition or from patients who have this condition but who are not experiencing inflammation or a current autoimmune inflammatory event. Based on the comparison of the spectrum slope and/or intercept, one or more actions may be carried out automatically or may be recommended, such as, without limitation, intervening in the patient's care; modifying a care program for treating the patient, or other actions as described herein. The method may be repeated continually, periodically, or as needed (or if desired) after a period of time, such as every day/night, weekly, monthly, or the like.

As described above, some embodiments of the technology described herein comprise a system or method utilizing nocturnal ultradian temperature rhythmometry and spectrum-analytic chronopharmaceutical decision-support to optimize management of a systemic autoimmune inflammatory condition in a human patient. One advantage of embodiments of the technology described herein versus conventional approaches to autoimmune inflammatory diseases, is that the thermometry aspect of the embodiments described herein do not require thermography or measurement of temperature of any affected joint or body area. Instead, embodiments described herein utilize our discovery that ultradian fluctuations in the expression levels of systemically-circulating inflammatory and anti-inflammatory cytokines that are associated with the so-called NLRP3-gene expression-related 'inflammasome' system in the body, which give rise to short time-scale fluctuations in central and peripheral temperature or in other ways influence neuroendocrine regulation of body temperature. Moreover, heretofore, it has not been practical under conventional processes to monitor such fluctuations on a continuous, high sampling-rate basis—on a time-scale shorter than that on which the fluctuations themselves occur. However, the particular processes and systems described by embodiments of the technology disclosed herein (such as the method described in connection to FIG. 3) overcome these conventional imitations. In particular, it is because of these novel arrangements of systems and the methods that improvements are realized, and not merely due to the use of miniature wireless RF beacons, nor the use of thermistor versus infrared means of thermometry.

As further described above, some embodiments include deriving a patient's temperature information via RF transmissions emitted by a temperature sensor-enabled beacon device, which may be worn by the patient. In particular, such embodiments may be configured for serially monitoring a patient having an autoimmune inflammatory condition on a longitudinal, nightly basis by means of a miniature wireless temperature-sensor-bearing short-range radio-frequency beacon. The beacon may be worn during nightly sleep by the patient in more or less continuous contact with axillary skin or other suitable region of the body, and may be configured to provide secure and periodic, frequent updates of temperature measurements acquired at a high sampling-rate (e.g., at least once per 10 minutes, once, per 5 minutes, or once per minute) from the patient via a computing device, such as a mobile device of the patient or other in-home caregiver or family member.

Figure 6C:
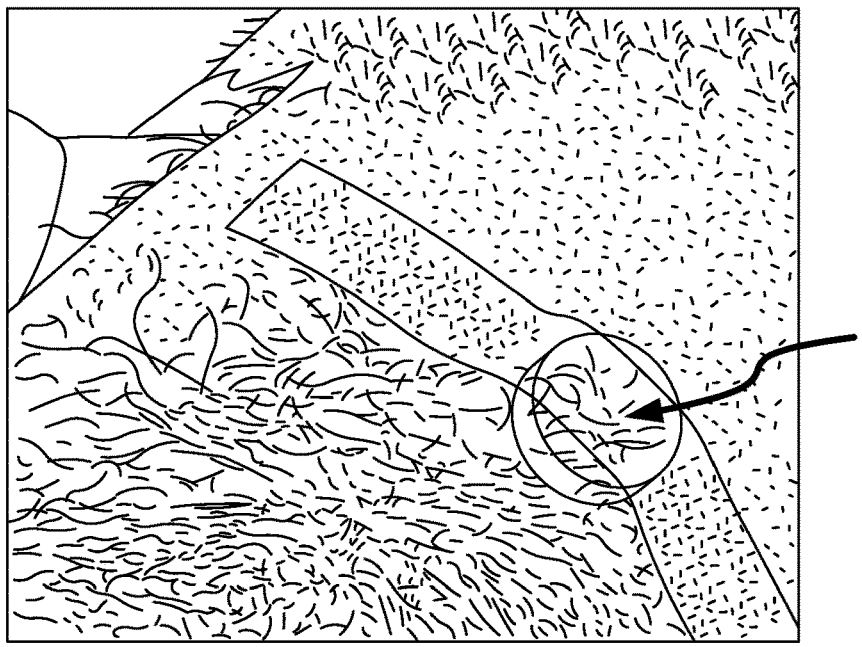
FIGS. 6A-6C depict an example RF (BLE-type) beacon suitable for use in embodiments of this disclosure.
Figure 6B:
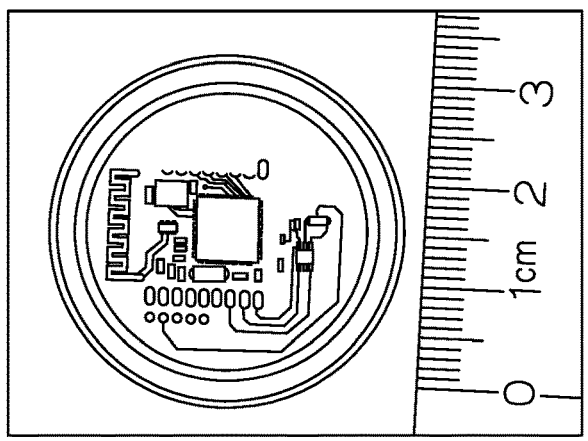
Figure 6A:
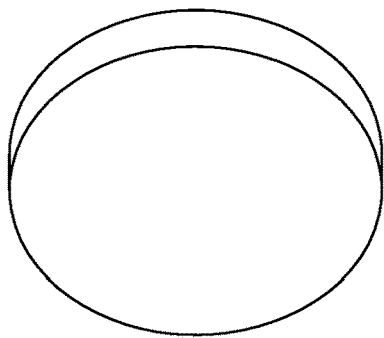

Accordingly, embodiments described herein provide a computerized system, methods, and computer-readable media for use in facilitating clinical decision making based on a patient's clinical situation. By way of example and not limitation, in one example embodiment, the entry of a wireless-communications-beacon-bearing patient into spatial proximity to an authorized user (which may include the patient) possessing a Bluetooth Low Energy (BLE)-enabled mobile device is detected on a software application (e.g., an app) running on the user's mobile device, such as application 143 described in connection to FIG. 1B. The beacon may be an RF or BLE-type beacon, for example, such as shown in FIGS. 6A-6C, and be associated with a particular patient. The beacon may broadcast or "advertise" an indication of the patient, such as a reference pointer corresponding to the patient's EHR information (or subset of patient EHR information) such that the indication is detected by the mobile device upon entry into the spatial proximity of the beacon. In this way, some embodiments provide or enable a context-aware provisioning of health information and health-related decision-support communications to a nearby human clinician or other caregiver, via a BLE-enabled mobile device.

In one embodiment, the beacon may be a tag or token that is affixed to the patient during nighttime sleeping, in an axillary region (e.g., in the armpit), for example (such as the example RF beacon device shown in FIGS. 6A, 6B, and 6C, further described herein). The software app may automatically activate upon receiving the indication or reference pointer beacon, or may be set to a listening mode. The app may respond, either automatically or by manual action by the user, to the RF or Bluetooth Low Energy (BLE) beacon advertisement. If the user is a clinician who is responsible for the care of, or a portion of the care of, the patient and has previously been so authorized, then the app may respond by binding to (or otherwise associating) the beacon and retrieving updated clinical and EHR or PHR information, from the EHR and/or PHR systems and, optionally, from the BLE beacon itself. Similarly, if the user is a family member or other authorized caregiver of the patient, then the app may likewise respond by binding to or associating the beacon and retrieving updated information pertaining to the patient.

In one embodiment, a transaction that establishes binding or association of the user's mobile device app to the patient's BLE beacon may soon thereafter trigger an online request to subscribe to a particular topic, concept, or set of interrelated concepts associated with a third party such as a patient, venue, or role by interrogating current problem list items or diagnoses, current ordered treatments or procedures, current medication list items, current associated health insurers or health plan indicia, current associated providers or pharmacies serving the BLE beacon-bearing patient, or otherwise selecting (i.e., tagging) one or more items of interest pertaining to the ongoing care of said patient. A health information system responds by dynamically retrieving a set of information associated with the combination of concepts that are associated with the indicated items. The set of associated information (or a portion of it, based on relevance or other criteria as described herein) may be made available on the mobile device for subsequent review or action. In some embodiments, the user's identity is authenticated by the information system and the user's access privileges are checked.

In some embodiments, the subscription duration is based on the spatial proximity to the beacon. For example, in one embodiment when the user's mobile device is no longer within range of the beacon, the app may no longer receive information about the patient. In some embodiments, spatial proximity is a factor in determining relevance when the system determines what subscribed-to information should be communicated to and/or displayed on the mobile device. Thus, where a user has "subscribed" (such as discussed above) to information about multiple patients (or multiple targets associated with beacons), the subscribed-to information may be ranked, prioritized, and/or analyzed for relevance based in part on proximity. For example, the subscribed-to information from patients not in proximity may not be provided (or not be presented on the user device) or this information may be presented below or after other subscribed-to information about patients who are in spatial proximity to the mobile device. In other words, for patient information (or targets) that a caregiver subscribes to, information about patients who are not present may not be presented to the user or may be presented after the information about patients who are present. In some embodiments, a user may selectively determine which subscriptions to keep or provide regardless of proximity, and which to de-subscribe-to or not display, based in part on proximity Thus it is contemplated that a user (or system administrator) may adjust the weighting of spatial proximity as a factor in determining relevance of the information displayed to the end user. For example, it is contemplated that in some instances critical information about a patient not present may be determined more relevant than certain information about present patients, and thus the critical information may be prioritized and/or ranked higher even though that patient is not in spatial proximity to the user's mobile device.

In some embodiments, when a clinical decision support event is subsequently triggered (either automatically or manually in various embodiments) regarding concepts to which the user has subscribed, the validity and then-current active status of the subscribed user's access privileges to the information are once again checked, and, if active and valid, the stored clinical information available for that patient and for the tagged-subscribed concepts that are relevant to the clinical decision support event are accessed. A system-generated link or access-means or message containing the relevant topical, concept-associated clusters of information are presented to the clinician user or to a consumer user. In one embodiment, this information is transmitted to the user's mobile device and presented on the mobile device via application software. Alternatively, the information may be contained in SMS text message or other general-purpose application software resident on the mobile device. In yet other embodiments, the information may be contained in an electronic mail message.

Some embodiments include a method for locating a nearest beacon within a plurality beacons in a health services facility. For example, one embodiment includes identifying a latest highest Received Signal Strength Indication (RSSI) value Bluetooth (or similar RF communication protocol) beacon associated with a highest RSSI value from within a set of latest scanned Bluetooth beacons. At least one average RSSI value may be computed for a predefined number of RSSI value detections associated with at least one Bluetooth beacon within a latest and previous set of scanned Bluetooth beacons. Thereafter, a highest average RSSI value Bluetooth beacon may be identified from within the latest and previous set of scanned Bluetooth beacons.

Conventional applications of RF beacons in healthcare settings typically have been directed to recipient users of health care services, such as patient wayfinding and patient check-in and tracking (for example, Connexient, Stanley, MySphera). In contrast, some embodiments described herein may utilize RF beacons for timely provisioning of context-, procedure-, venue-, and role-relevant electronic health record information and diagnostic and therapeutic decision-support to clinician or caregiver users who are providing care to the patient corresponding to the beacon.

In particular, conventional implementations of beacons that are worn or carried by a patient typically send a signal with a beacon identifier effectively saying "It is me, and I am here near you!" However, some embodiments described herein comprise enhanced beacons that may trigger transmission of relevant data related to the beacon bearer (e.g., a target patient affiliation with a plan or protocol; pending actions or decisions; allergies and medications and adherence data) from an electronic health records (EHR) computer system to the clinician's or caregiver's mobile device that detects the beacon. In some embodiments, the RF beacon itself may contain some synoptic salient items of patient care-related information, such as health plan indicia, insurance coverage status, major problem list categories and membership in treatment groups, either in the Minor number code that is part of the beacon device's identifier that is advertised via periodic RF signaling or in optional additional 'tag' codes that are contained in machine-readable storage in the beacon device (flash memory), which may be provided in an initial broadcast or provided subsequently after broadcasting a reference pointer and receiving a response by the mobile device.

Further, merely pushing alerts or offers of information to clinician users without referencing specific to patient data or context, which may include adherence and measurements history, may only result in clinician users' being bombarded with excessive push notifications that distract or cause "alert fatigue". This could induce providers to stop using an app or uninstall the app altogether. By contrast, push content that is timely and has relevant context, such as a reduced set of relevant and/or current information about the patient enables a smart, effective, efficient, personalized interaction between the clinician and the patient.

As described herein, confidentiality and privacy are of special concern with regard to healthcare and must be considered with any active messaging or communication means. In one aspect, embodiments utilizing RF beacons achieve greater privacy compared to RFID or similar technologies because beacon technology affords clinician user control of apps that leverage the beacons. Setting different proximity range/distance for different beacons can be set up by changing the broadcasting power of the beacons. For instance, a default setting may be −8 dBm, which may trigger configured rules (further described below) at approximately 2 meters on a BLE-enabled mobile device receiver. With beacons set to broadcast at 0 dBm power, rules may be triggered at approximately 8 m on the BLE-enabled mobile device receiver. At −16 dBm, rules may be triggered at approximately 0.5 meters. Such differences in proximity settings apply in different venues such as hospital intensive care units, individual exam rooms in physician offices, and group therapy conference rooms in outpatient psychiatry and addictions rehabilitation. Beacon device range settings are therefore germane not only to privacy and confidentiality protection, but also to engineering context-appropriate workflows that avoid presentation of excessively many choices or information that is not timely or in the clinician's or caregiver's immediate context.

In some embodiments, RF beacons may be predominantly enabled by Bluetooth Low Energy (e.g., BLE or Bluetooth 4.0). The beacons may be implemented in different formats, including small coin-cell-powered tag-type devices, USB sticks, etc. Another benefit of embodiments using RF beacon systems is that beacons primarily use mobile devices as the receiver system. Given that mobile devices and cellular networks have become ubiquitous, the receiver network is always-on and continuously connected. On the receiver device a mobile app (such as application 143 described below) may be utilized but, unlike conventional RF beacon systems often used in retail use-cases, there is no barrier in health plan and health care services venues to achieving high penetration and pervasive coverage. Clinicians in managed care and in accountable care organizations (ACOs) may be required according to the conditions of their employment contract to download a beacon receiver app and turn on location services for that app on their mobile device.

One of the considerable challenges in a conventional beacon deployment scenario is managing a large fleet of beacons, spread across multiple physical locations, grouped into different departments, and having different proximity messages attached to each group. Some embodiments described herein solve this problem of identifying groups of beacons by allocating a set of major numbers to each location and use the designated major number to manage a given group of beacons. For example, a provider organization may designate major number "87221" to the clinic location "West Village" and use that major number for every beacon of every patient whose care is primarily rendered at that clinic. Accordingly, to have a set of beacons trigger the same campaign, these embodiments may use the "UUID+ Major number" in combination to define a "context" and trigger content delivery, such as subscription updates of target patient information, based on that context.

However, even under this approach, this may be other problems. For example, in iOS, an app can only monitor a maximum of twenty regions. In particular, without re-engineering the UUID alone, the app is limited to about 12 'contexts' (analogous to 'regions' in proximity-based beacon-enabled scenario) to work with. Thus using region-type contexts to trigger 'protocols' or 'plans of care' or 'caresets' or 'care tickets' (analogous to 'campaigns' in proximity-based beacon-enabled scenarios) results in coarse-grained control.

Finer-grained control may be necessary in many situations to run personalized-medicine context-related care plans via specific beacons. Using BLE beacon Major numbers allows one to use only one dimension, such as individual identity or physical location, to define the scope of a personalized careset (campaign). In some instances, one may need more than one dimension to define the scope for specific caresets. For example, one may need to run personalized care plans based on patient (e.g., "MRN 1234567" encrypted in the beacon's Major number code or other beacon indicia) and clinical specialty or department (e.g., "mental health") worldwide, to enable context-aware care to be provisioned regardless where the patient presents herself for care. One can use the BLE beacon Major number for location or for department, but not both concurrently. Or one can use Major number as a patient identifier, but not for populations under care that are larger than 65,535 people.

To address these challenges, some embodiments described herein support the notion of "tags" that one can attach to different entities, such as Beacons, Rules, and Cards. Tags are flexible and afford finer-grained control than using beacon Major number control only. In embodiments using tags. As a beacon is deployed, it may be "tagged" with multiple properties concurrently, such as individual and group properties (e.g., the emitted reference pointer may comprise "MRN 1234567", which may be encrypted in the BLE beacon's Major number code and "St. John's bipolar depression group" encrypted in the BLE beacon's Minor number code). Authentication can be provided for wirelessly communicating data and/or services between the mobile device and at least one beacon out of a plurality of beacons and dispersed among patients.

Some embodiments include monitoring beacons and sending callbacks when a user mobile device is sufficiently close to the patient's wearable temperature-logging beacon, and in some instances when corresponding proximity rules are triggered. For example, one example embodiment actually reduced to practice uses iBeacons, which are Bluetooth Low Energy devices which keep emitting their identity at a predefined frequency, say every 500 milliseconds, also known as advertising interval. These signals are emitted at a fixed transmission power which is usually measured in dBm (dB-milliWatt). Typical values are −4 dBm, −8 dBm, −16 dBm. These signals can be detected by mobile device at distances up to approximately 70 m. In a typical deployment scenario where multiple beacons might be deployed as close as 50 centimeters from each other, a mobile device would receive signals from more than one beacon at a time. As described above, all of these beacons may be configured to have the same UUID which is common to the organization. However, each one would have a different identity as defined by two other numeric codes (Major and Minor) plus, optionally, additional tags. For example in one embodiment: UUID: 16-byte number typically common across an organization; Major: 2-byte number (0 to 65,535); Minor: 2-byte number (0 to 65,535); Tags: a list or vector of 4-byte numbers (0 to 4,294,967,295), each vector element denoting a concept or attribute or property or an entity with which the beacon-bearer has a relationship. In some embodiments, the combination of UUID, Major, and Minor will be unique, thereby making each beacon readily identifiable from other beacons.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the described technology. Thus for readability, we show and reference items in the singular (while fully contemplating, where applicable, the plural).

As shown in FIG. 1A, environment 100 includes computing system 130. In some embodiments, computing system 130 includes an adaptive multi-agent operating system, but it will be appreciated that computing system 130 may also take the form of an adaptive single agent system or a non-agent system. Computing system 130 may be a distributed computing system, a centralized computing system, a single computer such as a desktop or laptop computer or a networked computing system. Some embodiments of computing system 130 include a computer software stack, such as stack 121 of FIG. 1B, which in some embodiments operates in the cloud, as a distributed system on a virtualization layer within computing system 130. Furthermore, some embodiments of stack 121 include a distributed adaptive agent operating system as further described in connection with operating system 129 of FIG. 1B, which may be implemented as a platform in the cloud, and which is capable of hosting a number of software services, such as services 122-128 described in connection to FIG. 1B. Thus, in some embodiments, computing system 130 takes the form of a distributed adaptive-agent computing system or platform, which may further comprise a multi-agent computing system, as described herein.

In some embodiments, computing system 130 comprises a multi-agent computing system. Multi-agent computing system 130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control, which promotes the concept of autonomy.

In some embodiments, agents continually monitor events to proactively detect problems and leverage reasoning to react and dynamically alter a plan. In an embodiment, agents can be leveraged to determine concepts related or associated with the user-selected items of interest about a patient, and then prioritize those related items based on criteria such as user preferences, user history information, which can include information compiled from multiple users, staleness of the information item, condition of the third person, information items in the set of information items, the user device, or a significance-value associated with an information item. Thus for example, one or more agents may be used to determine which concepts a user, such as a healthcare provider, would want to see for a particular patient, given that patient's condition. To facilitate this, the one or more agents might employ information-set logic services 224 of FIG. 2B, in one embodiment. Accordingly, only those prioritized items, then, would be provided to the user's mobile device, in this embodiment.

System 130 comprises one or more processors operable to receive instructions and process them accordingly, and may be embodied as a single computing device or multiple computing devices communicatively coupled to each other. In one embodiment, processing actions performed by system 130 are distributed among multiple locations such as a local client and one or more remote servers. In one embodiment, system 130 comprises one or more computing devices, such as a server, desktop computer, laptop, or tablet, cloud-computing device or distributed computing architecture, a portable computing device such as a laptop, tablet, ultra-mobile P.C., or a mobile phone.

Figure 1B:
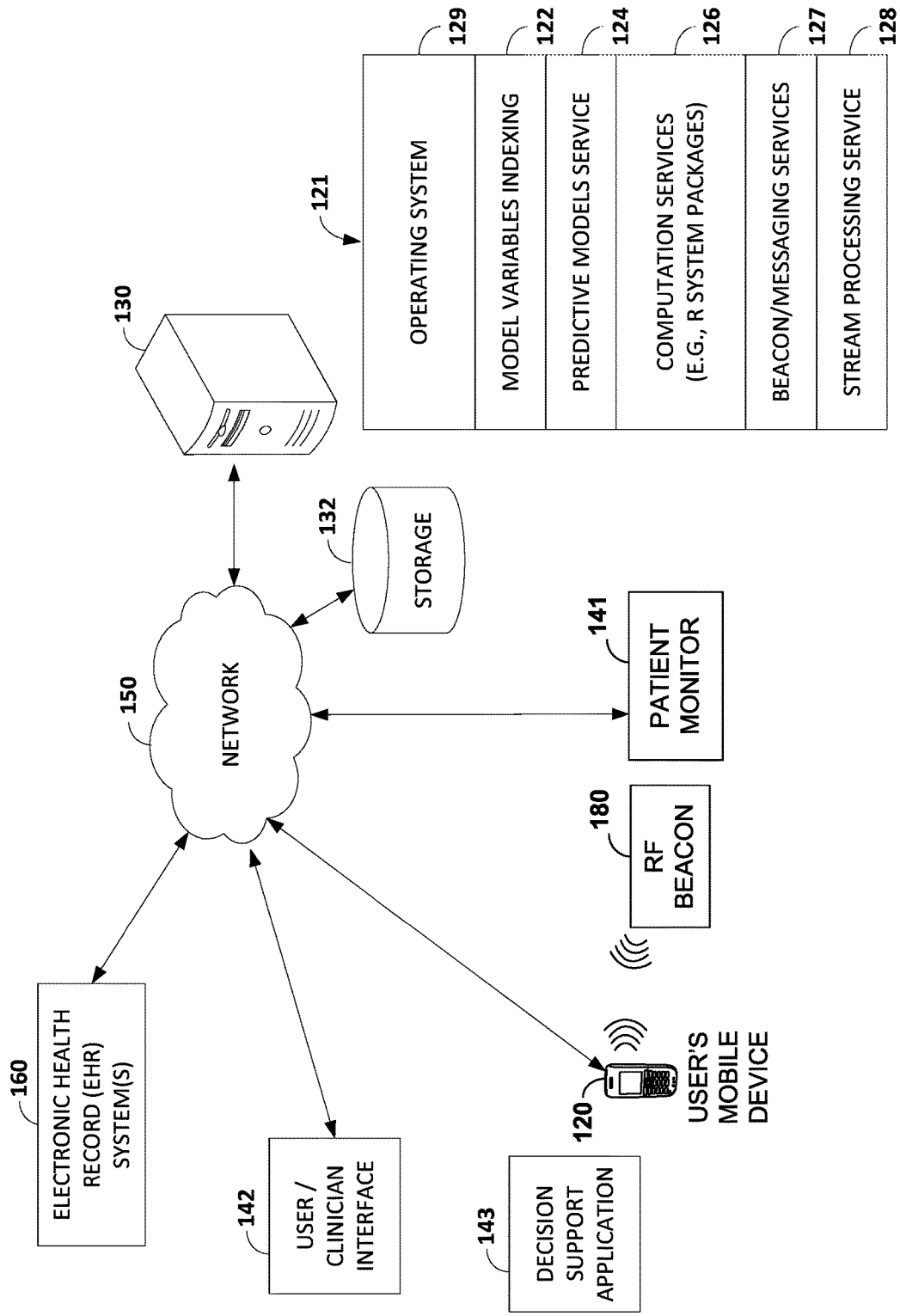
Figure 1C:
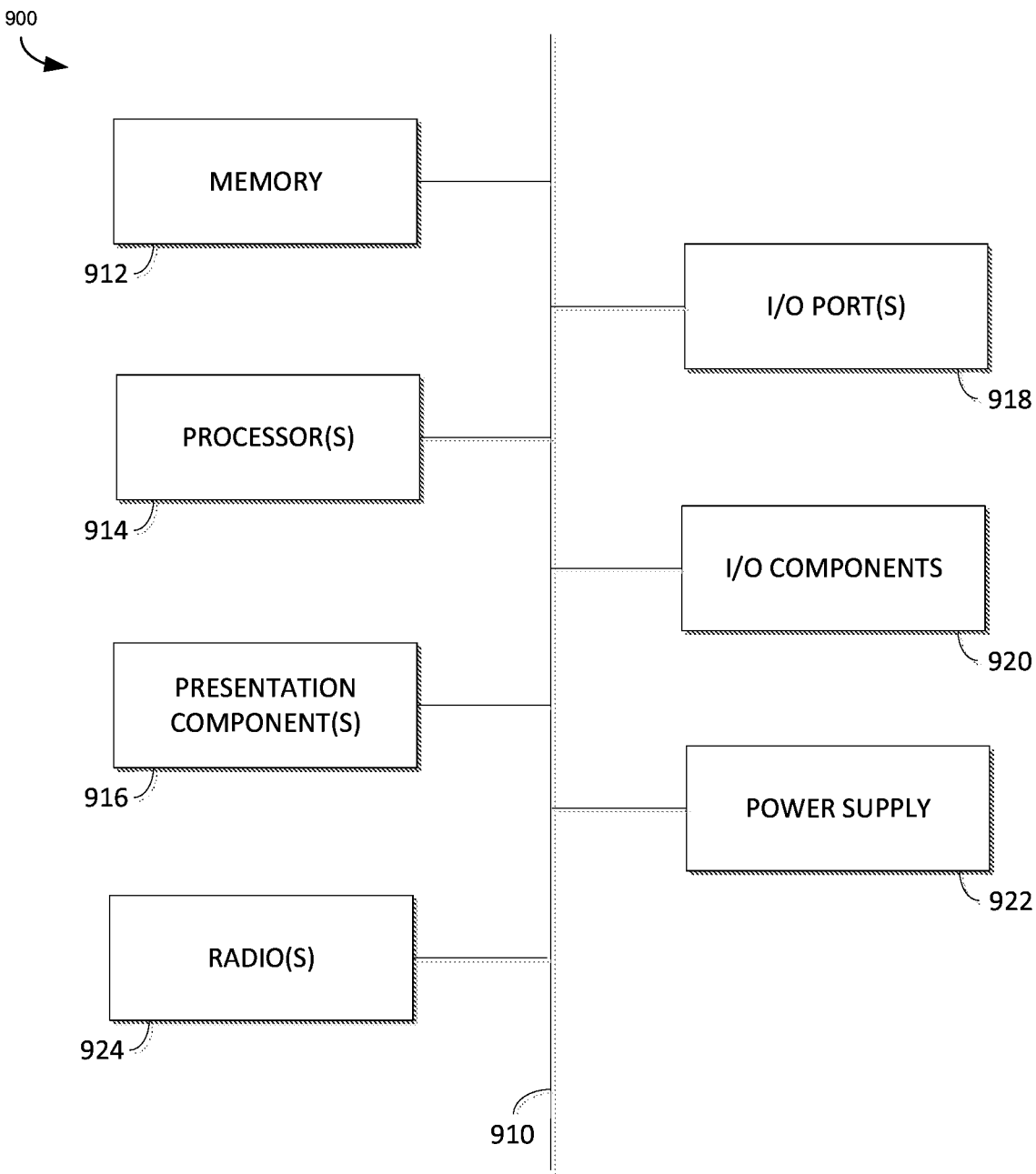

Turning briefly to FIG. 1C, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1C are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1C is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1C and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. Presentation component(s) 916 present data indications to a user or other device. Exemplary presentation components include a display device, speaker, printing component, vibrating component, etc.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1C is provided as one example of any number of suitable computer architectures, such as computing architectures that support local, distributed, or cloud-based software platforms, and are suitable for supporting computer system 120.

Returning to FIG. 1A, computing system 130 is communicatively coupled to information store or storage 132, described below, and communication network 150. Communication network 150 comprises a network or set of communicatively coupled networks that enable data and computer instructions to be communicated among the systems and devices coupled to the communication network 150. In an embodiment, network 150 includes the Internet, and may also include one or more intranets, which may be public or private. In some embodiments, network 150 comprises a cloud-computing network, which is known in the art as "the cloud" and may also include computing system 130. In an embodiment, network 150 includes a telecommunication network for communicating with a mobile device, such as a mobile phone.

Continuing with the embodiment depicted in FIG. 1A, communication network 150 is communicatively coupled to mobile device 120, server 140, Electronic Health Record Information system (EHR) 160, and Health Record Exchange, (HRE) 170; each of which is described below. In one embodiment, mobile device 120 is a mobile phone or tablet device able to receive data for example, SMS text messages, email, instant messages, or other data, and present information, or an indication that information is available, to a user. In one embodiment, mobile device 120 is a smart phone, such as an Apple® iPhone®, that includes an application program (an example of which is described in connection to FIG. 1B), and may be referred to herein as an "app." The app facilitates receiving the reference pointer, which in one embodiment comprises a communicated identifier or beacon, such as a BLE-type beacon comprising a UUID and/or and associated major and minor codes, additional tag codes and/or metadata, and presents information items, such as information about a third-party patient, to the user. In one embodiment, the app also provides user credentials for identification or authentication of the user, to server 140. In one embodiment, mobile device 120, or an app running on mobile device 120, is capable of communicating via a short-range RF protocol such as Bluetooth 4.0, ANT+, or other close-proximity RF protocol oriented to beacon-type signaling. Further embodiments of the app are discussed below in connection to FIGS. 1B and 5.

In some embodiments, as further described below, a user can be authenticated as a medical provider authorized to receive medical data based on a location of the user near the at least one beacon transponder located in association with a patient for which the medical data is provided. Mobile device 120 may be configured to enable the medical provider to record a medical procedure as a video via a digital camera (e.g., video cameras) integrated with the mobile device and make medical annotations while treating the patient. Such annotations can be voice annotations recorded by the mobile device. The annotations and the video can be securely stored in a server 140 and/or as a medical record in an electronic health record system 160 in association with the patient and can be made available for subsequent retrieval by authorized medical providers. In some embodiments mobile device 120 may be capable of bidirectional communication with a second screen or user interface in order to provide a larger viewing platform of the data and/or the services. In these embodiments, the second screen can be a display screen located within viewing proximity of the mobile device 120. The second screen can be, for example, be another computing a device such as a display screen of a smartphone, a laptop computer, a tablet computing device, a flat panel television, and a projector.

Server 140 receives requests originating from mobile device 120, for information identified by the reference pointer, such as subscribed-to information about a third-party patient, and provides that information, or a portion of that information, to the mobile device. In an embodiment, server 140 communicates with mobile device 120 through a mobile-device network, such as AT&T, Sprint, or Verizon, for example. In one embodiment, server 140 is included in computing system 130, and in one embodiment, server 140 is distributed across two or more of computing system 130, EHR 160, and a mobile device network. Thus, in some embodiments, server 140 may be distributed into any component that received a request for information from mobile device 120 and provides information to mobile device 120. Likewise, in some embodiments, computing system 130 includes server 140.

EHR 160 comprises the healthcare provider record system or electronic health record information, which in one embodiment includes electronic health records or medical records for a patient, a collection of patients, or a population. Additional examples of EHR 160 are described in FIG. 1B. HRE 170 comprises a health record exchange.

Example operating environment 100 depicted in FIG. 1A further includes a patient-monitor 165 and RF Beacon 180. Monitor 165 determines various physiological levels of a patient, such as for example, temperature, cardio, or respiratory information. In one embodiment, monitor 165 is embodied on RF beacon 180. In another embodiment, monitor 165 is embodied on a mobile computing device, such as a smart phone or base station that receives, records, monitors, or in some embodiments processes, physiological patient data received from RF beacon 180, such as the temperature information described herein. In one embodiment, monitor 165 takes the form of a bedside monitor such as bedside monitor 165 shown in FIG. 2B, such as may be found in a hospital for monitoring a patient's vital signs. In an embodiment, monitor 165 comprises a sensor or set of sensors worn by the patient, such as an RF beacon temperature sensor device worn by the patient. In one embodiment, monitor 165 is embodied as any patient monitor for monitoring information about a patient, such as patient monitor 141 shown in FIGS. 1B and 2A, and further described in FIG. 1B. In some embodiments, monitor 165 comprises or operates in conjunction with a decision support application, such as application 143 described in FIG. 1B, and may also include a user/clinician interface, such as interface 142 described in FIG. 1B.

In one embodiment, RF Beacon 180 comprises a wireless-communication apparatus worn on, carried about, or otherwise located in proximity to or on the person of a target, such as a patient. RF Beacon 180 may be configured to be capable of emitting RF signals having a modest range, which may be configurable such as from 1 meter to as much as 70 meters or more, indicating a physical proximity of the patient to one or more nearby wireless-communications enabled (such as BLE-enabled) mobile devices 120. In one embodiment, RF beacon 180 is capable of broadcasting a beacon that may be used to identify a particular nearby target (such as a patient) corresponding to the beacon and/or may be used to determine other information about the target, such as information corresponding to a plan or treatment group membership affiliations that are in-effect for the patient, and/or other care-related information, as described herein.

It should be noted that there are differences between location and proximity use-cases. In particular, location-determining technologies may utilize GPS, cell tower geo-location, WiFi, IP or MAC address (e.g., geoIP) for use cases such as driving directions, weather and atmospheric AQI exposures. Such technologies typically have a spatial resolution of tens of meters to kilometers. It is contemplated that some embodiments may utilize these technologies. But in contrast to location-determining technologies, proximity-determining technologies may utilize BLE, iBeacon, ANT+, RFID, or similar technologies and are more suitable for patient tracking, patient check-in, context-aware EHR information provisioning, and clinical decision support, and many of the other embodiments described herein. Such technologies typically have a spatial resolution of tens of centimeters to meters.

In some embodiments, as described herein, a caregiver-user or provider-user who is authorized to know of such target-patient information may be notified in near-realtime of the proximity of the patient and of the availability of said information on the user's BLE-enabled (or wireless-communications enabled) mobile device. Examples of RF Beacon 180 are shown in FIGS. 6A-6C. In particular, with reference to FIGS. 6A-6C, one embodiment of RF beacon 180 may take the form of a miniature beacon disc (FIGS. 6A-6B) which may be worn in an axillary region, such as the patient's armpit (FIG. 6C). In some embodiments, RF beacon 180 may be embodied as a computer, tablet computer, a mobile device such as a smartphone or other wireless-communication-enabled computing device, or any similar device capable of implementing beacon communications. RF Beacon 180 may comprise a single device or a may be a combination of devices, such as a beacon disc plus the patient's smartphone, or such as a beacon disc plus a wearable monitoring device such as a temperature monitor, an exercise tracker, or heartrate-measuring smartwatch, and may be stationary or mobile. In some cases, the beacon may be comprised of one component that is mobile (such as a beacon disc that is worn or carried by the patient) and another component that is stationary (such as a BLE-enabled bedside monitor, digital bathroom scale or blood pressure cuff).

One example of a beacon that can be implemented in accordance with one or more embodiments described herein is the "iBeacon." iBeacon is the trademark for the proximity system that Apple Inc. has referred to as "a class of low-powered, low-cost Bluetooth transmitters that can notify nearby iOS devices of their presence." The technology enables an iOS device or other hardware to send push notifications to iOS devices that are in close proximity, up to approximately 100 meters. Devices running the Android operating system, for example, can receive iBeacon advertisements but cannot emit iBeacon advertisements (i.e., embody a BLE 'central' role only and cannot serve as BLE 'peripherals'). Currently, the iBeacon operates on Bluetooth Low Energy (BLE), also known as Bluetooth Smart. BLE is also found on Bluetooth 4.0 devices that support dual mode. iBeacon uses Bluetooth low energy Proximity sensing to transmit a universally unique identifier (UUID) capable of being received by a compatible app or operating system that can be turned into a physical location or trigger an action on the receiving device.

Returning to FIG. 1A and with reference to FIG. 1B, which also includes RF Beacon 180, in some embodiments RF Beacon 180 is capable of communicating user information to a mobile device 120, which may be encoded as a reference to other information (i.e., a reference pointer) that identifies the set of information items related to a subscription or interest identified by a user, as described herein. As described above, in some embodiments, RF beacon 180 communicates information such as a reference pointer or identifier that functions as a reference to identify a target (e.g., a patient) associated with the RF beacon. In some embodiments, RF beacon 180 communicates information identifying the particular RF beacon, which is associated with the target (e.g., a particular patient) and thus references or points to information about the target. Thereafter, an app or other software on mobile device 120 may be used to determine a particular patient (or other target) identified by the information received from the RF beacon 180. The communication from the RF beacon 180 may be broadcasted, such as periodically, at intervals, or continuously or may be provided in response to a communication from the user mobile device 120. For example, user mobile device 120 may emit a signal or ping to awaken and identify RF beacons 180 in spatial proximity (such as within wireless communication range) of the user mobile device 120. In some embodiments, triggering rules and corresponding actions (described below) may be used to detect a particular beacon and/or to provide a certain information to a subscribing user or beacon-detecting mobile device.

Some embodiments herein may employ beacon context monitoring. A beacon context is a logical space which is formed by union of contexts (regions) of all beacons with same UUID or identifier and Boolean combination of Major number, Minor number, and, optionally, Tags. Some embodiments may be configured to monitor entering and exiting from Beacon context while a monitoring feature of an app (such as application 143 of FIG. 1B) is running in the foreground or, alternatively, is running in the background mode. Whenever the clinician or caregiver user enters or exits a beacon context, a communications service may send a callback to the app along with the identifier for the context. Beacon context monitoring is useful in identifying when the user is entering or exiting a venue where one beacon is present, such as an exam room where a single beacon-bearing patient is situated, or a venue where multiple beacons that bear a contextual relationship to each other are deployed, such as a conference room where the clinician user is presiding over a group therapy session for multiple patients concurrently.

Some embodiments herein may employ beacon ranging. Beacon ranging is a process of detecting the individual beacons 180 which are detectable by mobile device 120 inside a beacon context. For example, if there are 5 beacons currently present in a clinic or physician's office, the ranging call back from the communications service may return a list of all the 5 beacons along with their respective signal strength. This is useful in identifying relative distance from each beacon and automatically giving focus to the EHR information for the individual patient whose beacon is nearest. Alternatively, the clinician may manually bind to the EHR information of a patient associated with another beacon who is further away (or who is nearer but whose battery is more depleted than one or more other beacons; or whose bearer's clothing or purse or other objects partially obstructs the signal from that bearer's beacon, which therefore has a lesser signal strength for the mobile device of the clinician).

Some embodiments described herein may utilize a beacon camp-on/exit feature. In particular, the capability of beacon camp-on enables determining if a clinician or caregiver user (carrying a mobile device 120) has spent enough time within proximity of a beacon and, if so, declare the persistent proximity to be a camp-on connection to this particular beacon 180. In venues where the mobile device can range more than one beacon, a communications service may heuristically determine which of the beacons is sufficiently near to the user to constitute a potential group or beacon cluster. When proximity establishes a potential cluster, the attribute tags may be examined by the app to determine what Boolean intersections of attribute values exist among the beacons, if any. The discovery of one or more non-null intersections may cause the app to retrieve information pertaining to the discovered cluster or group. When the communications service notices that the user has moved significant distance from the beacon(s) and sufficient time has passed for the user to be unlikely to resume spatial proximity to the beacon(s), the communications service asserts a beacon exit. In both the cases, a delegate callback is sent from the communications service to the app along with reference to the beacon and the message corresponding to the camped-on beacon only needs to be displayed to the user. In the example of an outpatient health care clinic or physician office suite, if one beacon is carried or worn by various beacon-bearing patients, the communications service camps-on to individual patient beacons as the clinician user moves from one exam room to another. The corresponding relevant EHR media is displayed to the user one patient at a time, with no ambiguity about which patient and beacon are of interest at each moment. In some embodiments, a larger buffer radius between −75 dB and −80 dB may be employed to prevent CampOn/Exit cycles for occurring unwantedly.

Continuing with FIG. 1A, environment 100 also includes information store 132. Information store 132 stores information including data and executable code used to facilitate providing mobile-device updates of electronic health records. In some embodiments, this information includes, for example, user subscription information or information otherwise identifying a set of information items related to the information items indicated by the user; user-access permissions or authentication information; mobile-device identification codes; patient health records; healthcare provider records; parameters used by a distributed adaptive agent operating system including, for example, criteria for identifying and prioritizing the set of information items related to the information items indicated by a user; rules engine(s) and associated parameters for determining which information to provide to a mobile-device based on the indication received by a user; and user preferences.

Although shown as a single information store, information store 132 may comprise multiple separate dedicated information stores. For example in one embodiment EHR 160 may have a dedicated information store. In some embodiments, information store 132 comprises networked storage or distributed storage including storage on servers located in the cloud. Thus, it is contemplated that for some embodiments, the information stored in information store 132 is not stored in the same physical location. For example, in one embodiment, one part of information store 132 includes one or more USB flash drives or similar portable data storage media. Additionally, in some embodiments, data stored in information store 132 can be searched, queried, analyzed using system 130 or user/clinician interface 142 (described in FIG. 1B), which may be embodied within a software app running on mobile device 120 (such as application 143 described in FIG. 1B). In embodiments where information store 132 is distributed, portions of information stored in store 132 may be logically located behind a firewall or otherwise have limited access or require security validation for access.

Turning to FIG. 1B, an exemplary operating environment is provided and depicts aspects of an operating environments suitable for practicing some embodiments described herein. Operating environment 101 includes many of the components of operating environment 100 described above in connection to FIG. 1A, and provides additional perspectives of aspects of a suitable example operating environment. Just as with operating environments 100, other arrangements and elements can be used in addition to or instead of those shown in operating environment 101, and some elements may be omitted altogether for the sake of clarity. Further, as with operating environment 100, many of the elements described herein are functional entities that may be implemented as discrete or distributed components or in conjunction with other components, and in any suitable combination and location.

As described herein, some embodiments may be implemented as a system, comprising one or more computers and associated network and equipment, upon which a method or computer software programs or application(s) are executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environments 100 and 101, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example environment 101, it is contemplated that in some embodiments functionality of these components can be shared or distributed across other components.

With reference to FIG. 1B, example operating environment 101 includes one or more electronic health record (EHR) systems, such as EHR system(s) 160 communicatively coupled to network 150, which is communicatively coupled to computer system 130. In some embodiments, components of environment 101 that are shown as distinct components may be embodied as part of or within other components of environment 101. For example, EHR system(s) 160 may comprise one or a plurality of EHR systems such as hospital EHR systems, health information exchange EHR systems (such as health information exchange 170 shown in FIG. 1A), clinical genetics/genomics systems, ambulatory clinic EHR systems, psychiatry/neurology EHR systems, insurance, collections or claims records systems; and may be implemented in or as a part of computer system 130. Similarly, EHR system(s) 160 may perform functions for two or more of types of EHR systems (not shown). EHR system(s) 160 also may include records of physiological variables or other patient information obtained via one or more measurement apparati, tests, or screenings, such as patient monitor 141 (or bedside monitor 165 of FIG. 2B), and may perform functions for two or more of types of EHR systems (not shown). In an embodiment, EHR system(s) 160 includes historical claims data for health services, apportionment data, and related health services financial data.

In some embodiments of the technologies described herein, aspects of decision support for patient care may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1B, network 150 may comprise the Internet, and/or one or more public networks, private networks, other communications networks such as a cellular network, or similar network(s) for facilitating communication among devices connected through the network. In some embodiments, network 150 may be determined based on factors such as the source and destination of the information communicated over network 150, the path between the source and destination, or the nature of the information. For example, intra-organization or internal communication may use a private network or virtual private network (VPN). Moreover, in some embodiments items shown communicatively coupled to network 150 may be directly communicatively coupled to other items shown communicatively coupled to network 150.

In some embodiments, operating environment 101 may include a firewall (such as depicted in FIG. 1C) between a first component and network 150. In such embodiments, the firewall may reside on a second component located between the first component and network 150, such as on a server 140

(not shown in FIG. 1B), or reside on another component within network 150, or may reside on or as part of the first component.

Embodiments of electronic health record (EHR) system(s) 160 include one or more data stores of health-related records, which may be stored on storage 132, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as information received from RF beacon 180, a physiological sensor, such as a wearable sensor, or monitor 141, such as a bedside, laboratory, or in-home patient monitor (e.g., bedside monitor 165 of FIG. 2B) or sensors, for example, such as monitor 141.

Example operating environment 101 further includes a user/clinician interface 142 communicatively coupled through network 150 to an EHR system 160. In some embodiments, user/clinician interface 142 also may be directly or indirectly communicatively coupled to RF beacon 180 (not shown). For example, as further described herein, in some embodiments, user/clinician interface 142 may be part of an application, such as decision support application 143, and may reside on computing system 130, mobile deice 120 (or may be a cloud-based application accessed via mobile device 120) for viewing information about a patient identified via information receive d from RF beacon 180. Similarly, user/clinician interface 142 may be communicatively coupled to RF beacon 180 for assigning RF beacon 180 to a particular patient (or other target) or for configuring settings or parameters, or receiving diagnostic or status information about the RF beacon 180, such as battery life, communication range (e.g., broadcast power), or operational settings (e.g., how often to broadcast or a particular protocol or encoding scheme for a reference pointer information communicated by RF beacon 180). Examples of user/clinician interfaces 142 for use with RF beacon 180 are illustratively depicted in FIGS. 5A-5D.

As described previously, some embodiments of mobile device 120 or computing system 130 may support operation of a decision-support software application 143 (or app) for receiving information from RF beacon 180 and/or using that information to receive additional, relevant information about a target identified by RF beacon 180. In one embodiment, software application 143 or app is includes or operates in conjunction with user/clinician interface 142, and comprises a software application, or set of applications (which may include programs, routines, functions, or computer-performed services) residing on a computing device such as computing device 130, mobile device 120, or may be distributed in the cloud and/or on other client computing device(s), such as a personal computer, laptop, smartphone, tablet, or other mobile computing device. In an embodiment, the application 143 is a Web-based application or applet, and may be used to provide or manage user services provided by an embodiment of the technologies described herein, such as to facilitate receiving information from RF beacon 180 and in some embodiments, then receiving additional relevant information referenced by the information received from RF beacon 180. In some embodiments, application 143 comprises a computerized decision support tool and may include aspects of user/clinician interface 142.

In some embodiments, application 143 and/or user/clinician interface 142 facilitates accessing and receiving information from a user or health care provider about a specific patient or set of patients, according to the embodiments presented herein. Embodiments of application 143 and/or user/clinician interface 142 also may facilitate accessing and receiving information from a user or health care provider about a specific patient, caregiver, or population including temperature information, historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 143 and/or user/clinician interface 142 also facilitates receiving orders, staffing scheduling, or queries from a user, based on the results of monitoring and/or forecasted outputs, which may in some embodiments utilize user/clinician interface 142.

In particular, user/clinician interface 142 facilitates receiving from a user, an indication of a particular topic, concept or group of interrelated concepts for which the user, or another user, desires to receive updated information. For example, in one embodiment, user interface 142 is capable of receiving a selection by a user of items of interest about a third-party patient, for which the caregiver-user desires to monitor by receiving updates of information related to the selected items of interest on the user's mobile device. In one embodiment, user interface 142 facilitates receiving temperature information for a patient. In some embodiments, user/clinician interface 142 may be embodied as a touch screen, a display, an electronic clipboard or chart, tablet computer, laptop computer, bedside patient monitor, a mobile device, or any similar device capable of receiving input from a user of items of interest about a patient, topic, or concept, including for example a speech-recognition user interface. Interface 142 may be a single display on a single device or a combination of devices, which may be distributed at different locations, and may be stationary or mobile.

One embodiment of interface 142 takes the form of a graphical user interface and application, which may be embodied as part of a software application (e.g., a decision support application 143 operating on or accessed via mobile device 120 or computing system 130) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, user/clinician interface 142 includes a Web-based application (which may take the form of an applet or app) or set of applications usable to manage user services provided by an embodiment of the technologies described herein.

In some embodiments user/clinician interface 142 and/or application 143 is configured to display information about an RF beacon 180. For example, this may include information concerning the beacon's battery status, RF signal strength, and clinical conditions or treatments groups that are associated with this beacon for the beacon's bearer/user. FIG. 5D depicts an example user/clinician interface 142 on a mobile device 120 (not shown) for ascertaining the properties of a BLE beacon, for purposes of device parameters review and/or troubleshooting. In one embodiment, interface 142 and/or application 143 is configured to display information associated with a beacon's periodic RF broadcasts of its presence to mobile-devices 120 (or other wireless-communication enabled devices) for detecting the beacon in the vicinity.

In some embodiments, the user interface 142 includes a pushbutton-style switch on a miniature beacon disc to enable placement of the beacon disc into an "Airplane Mode" discontinuing RF transmissions while in aircraft or other locations where RF signaling is prohibited, and in one embodiment, user interface 142 includes or facilitates other input means such as a keyboard, mouse, pad, voice-recognition module, or other means for receiving, from a user, an indication of information items or commands.

Example operating environment 101 includes patient monitor 141 communicatively coupled through network 150 to an EHR system 160. In an embodiment, patient monitor 141 communicates via network 150 to computer 130, mobile device 120, and/or user/clinician interface 142. The term monitor is used broadly herein, and it is contemplated that in some embodiments, monitor 141 may not perform monitoring but may receive information about physiological parameters which may be measured, observed, or otherwise recorded, such as information received from RF beacon 180. Embodiments of monitor 141 may comprise one or more sensors, an interface component, and/or processing/communications component (not shown). In an embodiment of monitor 141 comprises or operates in conjunction with one or more sensor components operable to acquire clinical or physiological information about a patient, such as various types of physiological measurements, physiological variables, or similar clinical information associated with a particular physical or mental state of the patient, and which may be acquired periodically, continuously, as needed, or as they become available, and may be represented as one or more time series of measured variables. In one embodiment, monitor 141 and/or RF beacon 180 includes a thermistor-based sensor for measuring body temperature of a patient. In one embodiment, monitor 141 comprises sensors for obtaining (and in some instances pre-processing or interpreting) temperature, non-invasive recording of vital signs, or other physiological or clinical variables, which may be obtained continuously, periodically, or at irregular intervals. For example, in an embodiments monitor 141 comprises a patient monitoring system such as Sotera ViSi®, Finapres® NOVA™, or Covidien ZephyrLIFE™. In some embodiments, monitor 141 comprises patient bedside monitor, such as bedside monitor 165 of FIG. 2B, which may be used in a hospital setting. In an embodiment, one or more sensor components of monitor 141 may comprise a user-wearable sensor component, such as some embodiments described in connection to RB beacon 180, or sensor component integrated into the patient's environment. Examples of sensor components of monitor 141 include or operate with sensor(s) positioned on an appendage (on or near the user's head, attached to the user's clothing, worn around the user's head, neck, leg, arm, wrist, ankle, finger, armpit, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the technology disclosed herein may be received from human measurements, human observations, or automatically determined by sensors in proximity to the patient. For example, in one embodiment, a nurse periodically measures a patients' blood pressure and enters the measurement and/or observations via user/clinician interface 142. In another example, a nurse or caregiver enters one or more progress notes for an in-patient via user/clinician interface 142. Similarly, values for vital signs variables may be entered via user/clinician interface 142.

Examples of physiological variables monitored by monitor 141 can include, without limitation, temperature, vital signs variables, such as heart rate (bradycardia and tachycardia) and blood pressure (hypotension and hypertension) and oxygen saturation (peripheral desaturation), as described herein. Additionally, in some embodiments physiological variables monitored by monitor 141 may include, by way of example and not limitation, central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making In an embodiment, a monitor such as 141 comprises a sensor probe, such as an EEG probe, and a communication link that periodically transmits identification information and probe data to EHR 160, so that the time series of monitored values is stored thereby enabling the patient manager to determine a physiological variable decision statistic. In an embodiment, monitor 141 collects raw sensor information, such as optical sensor 184, and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, user/clinician interface 142, and/or computer system 130.

Embodiments of monitor 141 may store user-derived data locally or communicate data over network 150 to be stored remotely. Some embodiments of monitor 141 include a monitor interface, which may be embodied as user/clinician interface 142 or a separate monitor user interface, and may further include I/O such as buttons and sounds emitted from the monitor 141, its firmware or software application or app operating on a user's mobile device 120 or computer system 130, and in an embodiment may facilitate uploading of measured (or recorded, or otherwise received) information from measurement device 141 to EHR 160 or computer system 130.

Additionally, some embodiments of monitor 141 include functionality for processing patient-derived information locally or for communicating the information to computer system 130, where it may be processed. In some embodiments, the processing may be carried out or facilitated by one or more software agents, as described herein. In some embodiments the processing functionality, performed on monitor 141 and/or computer system 130 includes pre-processing and/or signal conditioning, such as removing noise or erroneous information (e.g., trimming silent leaders or trailers in a time series), demeaning, and de-trending time series information.

Example operating environment 101 further includes computer system 130, which may take the form of one or more servers (such as server 140 of FIG. 1A) or mobile device(s) (such as mobile device 120 of FIG. 1A), and which is communicatively coupled through network 150 to EHR system 160, and storage 132.

Computer system 130, an embodiment of which is described in connection to FIG. 1A, may comprise one or more processors operable to receive instructions and process them accordingly, and may be embodied as a single computing device or multiple computing devices communicatively coupled to each other. In one embodiment, processing actions performed by system 130 are distributed among multiple locations such as one or more local clients and one or more remote servers, and may be distributed across the other components of example operating environment 101. For example, aspects of user/clinician interface 142 and/or software application 143 may operate on or utilize computer system 130. Similarly, a portion of computing system 130 may be embodied on user interface 142, application 143, and/or EHR system(s) 160. In one embodiment, system 130 comprises one or more computing devices, such as a server, desktop computer, laptop, or tablet, cloud-computing device or distributed computing architecture, a portable computing device such as a laptop, tablet, ultra-mobile P.C., or a mobile phone.

In some embodiments, computer system 130 is a computing system made up of one or more computing devices. In some embodiments, computer system 130 includes one or more software agents, and in an embodiment includes an adaptive multi-agent operating system (an example of operating system 129, described herein), but it will be appreciated that computer system 130 may also take the form of an adaptive single agent system or a non-agent system. Computer system 130 may be a distributed computing system, a data processing system, a centralized computing system, a single computer such as a desktop or laptop computer or a networked computing system.

Embodiments of computer system 130 include computer software stack 121, which in some embodiments operates in the cloud, as a distributed system on a virtualization layer within computer system 130, and includes operating system 129. Operating system 129 may be implemented as a platform in the cloud, and which is capable of hosting a number of services such as 122, 123, 124, 126, 127, and 128. Some embodiments of operating system 129 comprise a distributed adaptive agent operating system. Embodiments of services 122 through 128 may run as a local services or may be distributed across one or more components of operating environment 101, in the cloud, on one or more personal computers or servers such as system 130, mobile device 120 (or a computing device supporting communications of RF beacon 180) and/or a computing device running interface 142 or application 143. In some embodiments, services 122 through 128 take the form of one or more software programs or routines, which may be employed by a software agent, and in some embodiments one or more of services 122 through 128 is embodied as a software agent. In some embodiments, interface 142 and/or application 143 operate in conjunction with software stack 121 and/or one or more services 122 through 128.

Model variables indexing (or mapping) service 122 may facilitate retrieving patient physiological variables, which may include frequent item sets, extracting database records, and/or cleaning the values of variables in records. For example, service 122 may perform functions for synonymic discovery, indexing or mapping variables in records, or mapping disparate health systems' ontologies, such as determining that a particular medication frequency of a first record system is the same as another record system. Predictive models service 124 comprises computing services or routines for forecasting likelihood of respiratory deterioration, which may be developed and implemented according to the method described in connection to FIG. 2. In some embodiments, services 122 and 124 may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages psd, for performing power spectral density estimates; and multicomp, for determining linear hypotheses in parametric models. Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 4A-4C. Computation services 126 also may include services or routines for utilizing one or more prediction models such as described in connection to FIG. 2 and the example computer program routines illustratively provided in FIGS. 4A-4C. In some embodiments, computation services 126 use EHR system(s) 160, model data and model storage services (not shown), and/or other components of example operating environment 100, and may also include services to facilitate receiving and/or pre-processing physiological data. For instance, model data and model storage services may be utilized to perform services for facilitating storage, retrieval, and implementation of the forecasting models described herein and of the data used in the models.

Beacon/messaging services 127 generally includes computer-related services, applications, programs, or computer routines for operating or communizing with one or more RF beacons 180. In some embodiments, beacon/messaging services 127 includes one or more of the following services: authentication services, access control permissions services, information-set logic services, message assembly services, and update subscription registry.

Authentication services and access control permissions services may provide security and privacy related services for validating transactions with a mobile device 120 (or a wireless-communications enabled RF beacon reading device) including subscription requests, such as described in connection to subscription service 190 of FIG. 2A. For example, in some embodiments services 122 and 124 facilitate validating user or patient credentials information. Information-set logic services 124 facilitates determining the set of information items related to the patient to communicate to a user/subscriber, and may further facilitate ranking and prioritizing the items. In some embodiments, services 124 also facilitates determining the subset of information item for communication to or presentation to a user/subscriber. In some embodiments the services 124 operates in conjunction with message assembly services 126 for determining the subset of information items. Message assembly services 126 facilitates the preparation or receipt of information communicated to or from mobile device 120 (or a wireless-communications enabled RF beacon reading device). Update subscription registry service 128 facilitates maintaining the registry of subscriptions such as described in connection to subscription service 190 in FIG. 2A. In some embodiments, subscription registry services are carried out my updates subscription service 190.

Some embodiments of stack 121 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 121 may further comprise one or more stream processing service(s) 128. For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the present technology also may be used in conjunction with Cerner Millennium®, Cerner CareAware® (including CareAware iBus®), Cerner CareCompass®, or similar products and services.

Example operating environment 100 also includes storage 132 (or data store 132), an example embodiment of which is described in connection to FIG. 1A. In some embodiments, storage 132 includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 132 comprises the data store(s) associated with EHR system(s) 160. Further, although depicted as a single storage data store, data store 132 may comprise one or more data stores, or may be in the cloud.

Figure 2A:
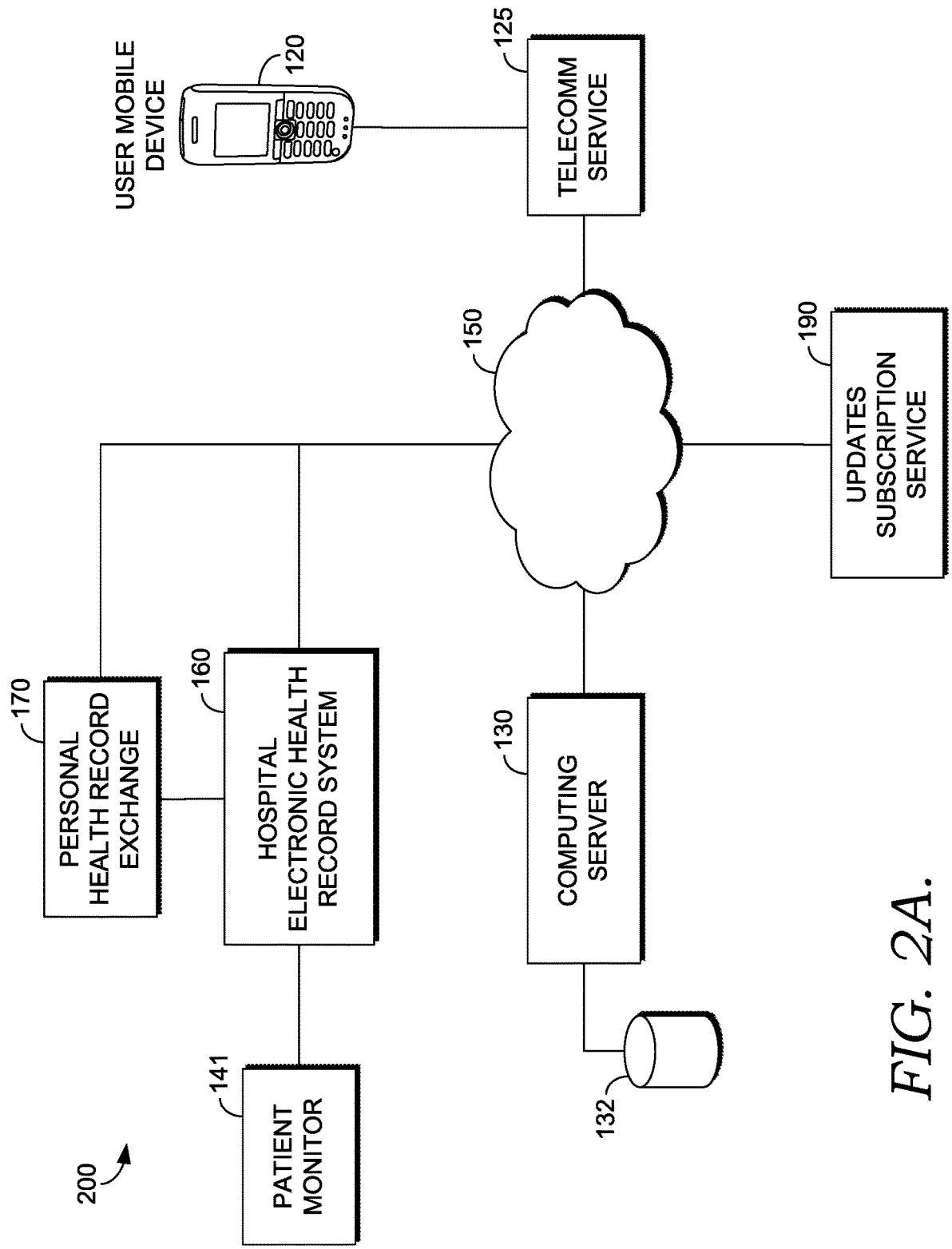
FIGS. 2A and 2B depict aspects of illustrative operating environments suitable for implementing embodiments of the disclosure also showing telecom or mobile data services.
Figure 2B:
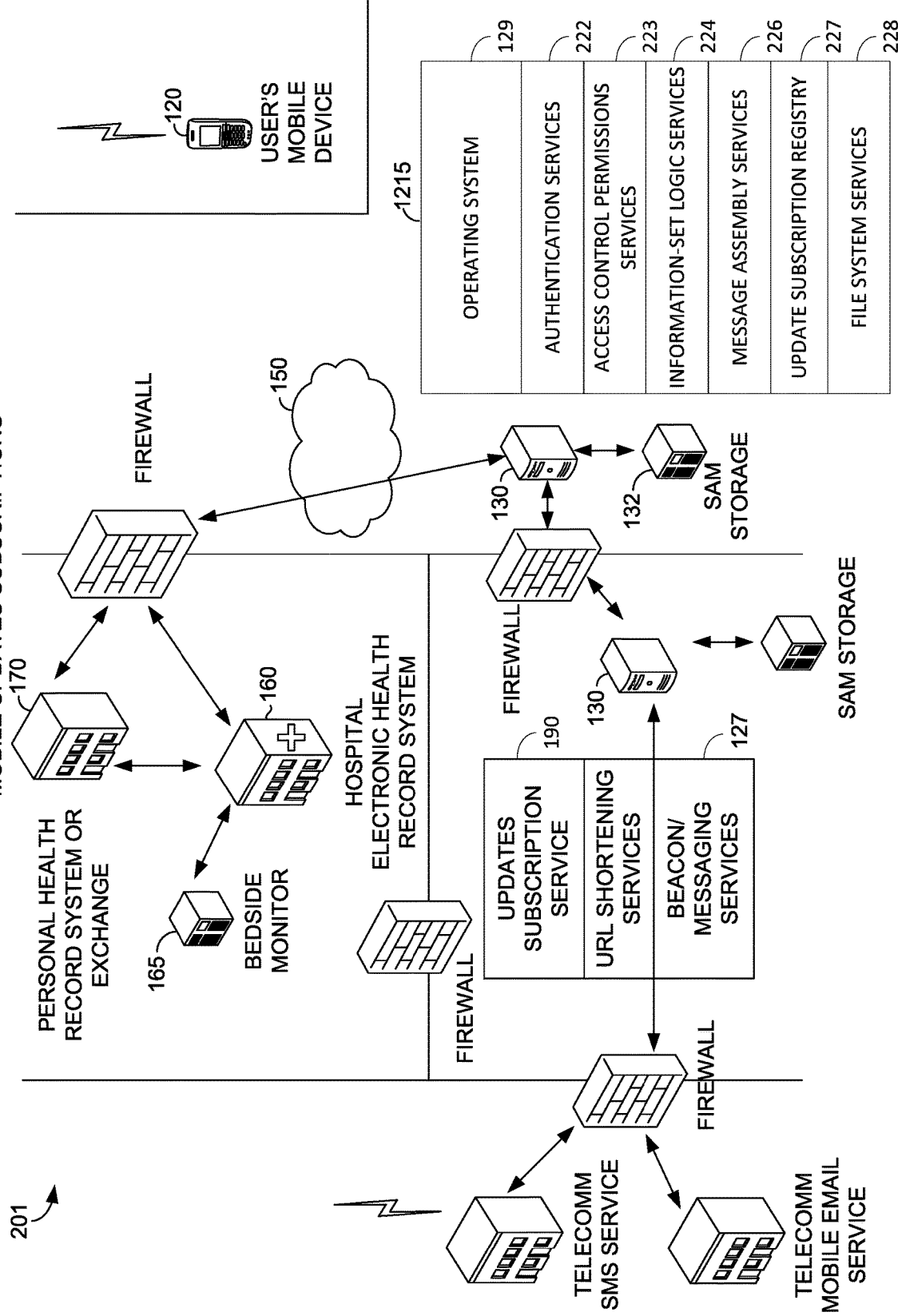

Turning now to FIGS. 2A and 2B, FIG. 2A depicts another example operating environment 200 suitable for practicing an embodiment of the technologies described herein. In environment 200, mobile device 120 is communicatively coupled to telecom service 125. In some embodiments, telecom service 125 is provided by a mobile service provider such as AT&T, Sprint, or Verizon, for example, and includes mobile web or data service, mobile e-mail service, mobile SMS service, or a combination of these services. Environment 200 also includes updates subscription service 190. Subscription service 190 facilitates user-subscription functionality and in some embodiments includes an update subscription registry, which includes information specifying subscriptions and registers information updates for subscribed-to concepts, topics, groups of concepts, or information items. In one embodiment, the update subscription registry is used to determine which updates a user's mobile device 120 should receive, based, in one embodiment, on information about available updates and, in one embodiment, also based on information about which updates the mobile device has already received.

In one embodiment, subscription service 190 receives information from mobile device 120 specifying information about the user's mobile device, bandwidth, data connection speed, user feedback, and other information in addition to information related to the reference pointer. Subscription service 190 uses this additional information for managing the communication of a subset of information items, from the set of information items identified by the reference pointer, to the mobile device, in one embodiment. For example, subscription service 190 may throttle the information or only provide the most important information items, where a mobile device's data connection is limited. In one embodiment, the communication is managed by computing system 130 or a server (not shown in FIG. 2A, such as server 140 in FIG. 1A), and in one embodiment, the information received from mobile device 120 is used to determine the priority or ranking of the information items in the set of information items.

In some embodiments subscription service 190 receives a subset of information items related to those items subscripted to (or indicated by) a user, and facilitates the communication of the subset of information items to the mobile device. For example, subscription service 190 may prepare for sending via SMS, a message containing a secure hyperlink to the subset of information items, in an embodiment. In an embodiment, subscription service 190 functions as a server, such as server 140, and in one embodiment, subscription service 190 is part of server 140 (FIG. 1A) or part of computing system 130. For example, in an embodiment subscription service 190 takes the form of one or more software programs or routines, or software agents residing on computing system 130.

In one embodiment, subscription service 190 receives requests from a mobile device for information associated with the reference pointer. In one embodiment, subscription service 190 manages the security and authentication of a user's mobile device when a request is received or before third-party information is provided to the mobile device. In some embodiments, subscriptions may expire. For example, a user may only be permitted to view data about a particular patient for a limited duration of time. Or after a period of time, information about a particular patient may no longer be useful (e.g., if the patient has recovered and is no longer being monitored.) It is contemplated that in such embodiments, subscription service 190 manages the subscription lifetimes, thereby facilitating individual subscriptions to expire or be renewed. In one embodiment, subscription service 190 throttles information provided to mobile device 120. In one embodiment, the throttling is intelligently determined using a rules engine or agent, such that only the most important information is updated as it becomes available, and less important information items are updated periodically, such as once every hour. In one embodiment, subscription service 190 throttles information so as to conserve bandwidth usage.

FIG. 2B provides as another example operating environment 201 suitable for practicing embodiments of the technologies disclosed herein and includes many of the same components described in connection to FIGS. 1A-1B and 2A. In particular, example operating environment 201 includes one example embodiment of a computing system 130 having a stack 1215 with operating system 129 (such as described in FIG. 1B) and beacon/messaging services including: authentication services 222, access control permissions services 223, information-set logic services 224, message assembly services 226, update subscription registry service 227, and file system services 228, examples of which are described in connection with beacon/messaging services 127 of FIG. 1B.

Figure 3:
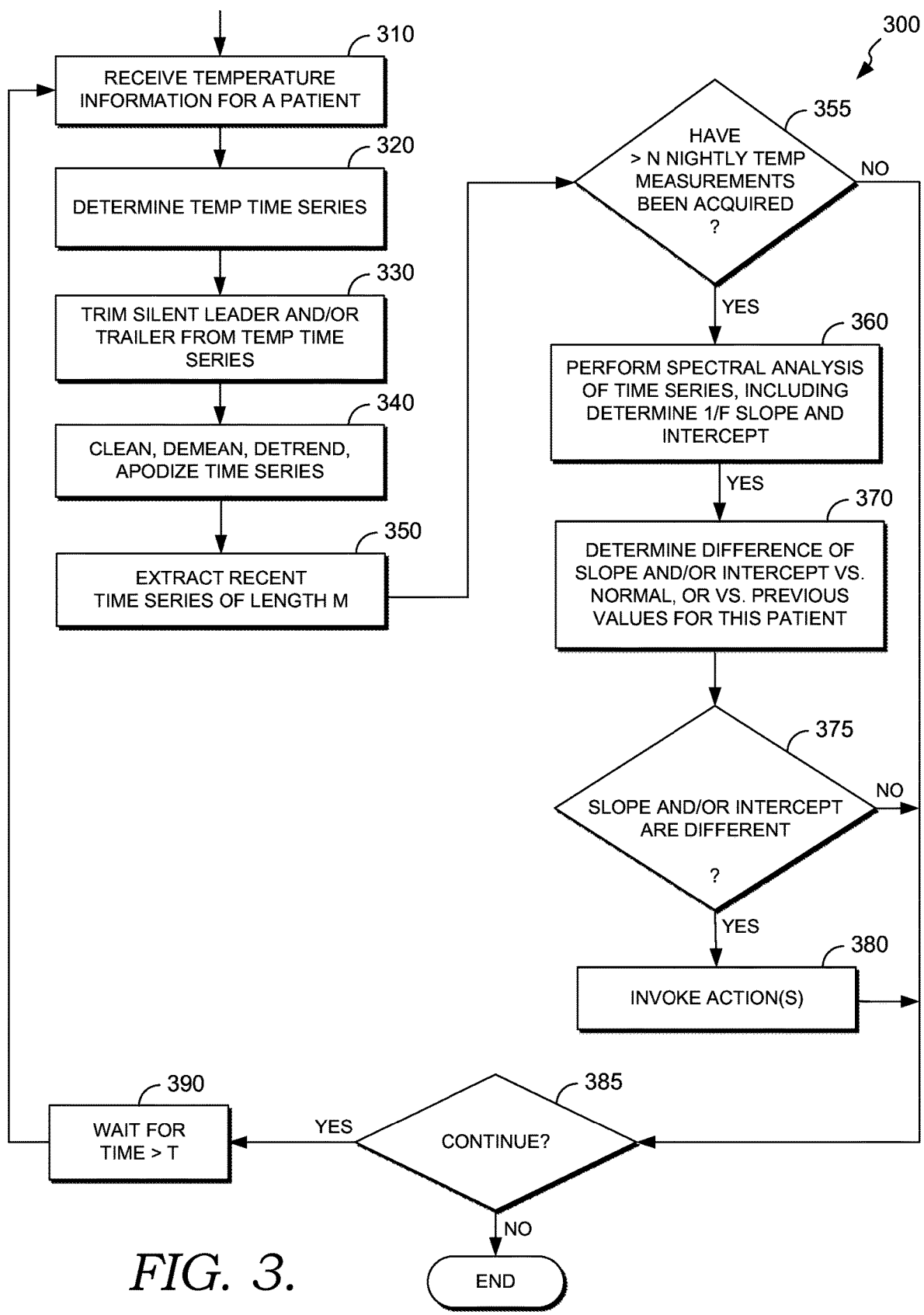
FIG. 3 depicts a flow diagram of an example method for providing clinical decision support for a patient having Rheumatoid Arthritis, in accordance with embodiments of this disclosure.

Turning now to FIG. 3, a flow diagram is provided that illustrates a method 300 for determining that a patient is experiencing or will experience an autoimmune inflammatory event or episode, and if needed, implementing one or more response actions based on the determination. At a high level, and a described above, embodiments of the technologies described herein may first determine and utilize a time series of nocturnal or ultradian core or axillary temperature information about a patient, which may be determined from a temperature sensor-enabled beacon device, such as RF beacon 180, described in FIG. 1B. From this time series of temperature information, a spectrum analysis is performed to determine a spectrum slope and intercept in a frequency passband. A comparison then may be performed based on the current or recent spectrum slope and intercept versus a baseline value(s) for a reference patient or from the patient's own previous value(s), and used to generate a score indicating an autoimmune inflammatory event or likelihood of future autoimmune inflammation by the patient. The score (or the result of the comparison) may include a statistical probability or prediction, which may be used by a decision support tool to determine and/or invoke a particular action in response to the score. For example, based on the generated score (or results of the spectral analysis and comparison, as described herein), one or more actions may be carried out, as further described herein.

With reference to FIG. 3, circadian and ultradian changes in the metabolism or nocturnal secretion of endogenous corticosteroids (decrease) observed in rheumatoid arthritis (RA) patients are responsible, in part, for the time-dependent changes in a human body's inflammatory response and related early morning clinical symptoms of the disease. Melatonin (MLT), another circadian nocturnal hormone that is the secretory product of the pineal gland under the brain, has been implicated in the time-dependent RA inflammatory reaction with effects that are opposite to those of corticosteroids. As a consequence, altered functioning of the hypothalamus-pituitary-adrenal (HPA) axis (morning-decreased corticosteroid production) and of the pineal gland (night-increased MLT production) found in RA patients, are important factors in the appearance and perpetuation of the clinical circadian symptoms of the disease. Consistently, human pro-inflammatory Th1-type cytokine production (related to MLT stimulation) exhibits a diurnal rhythmicity with peak levels during the night and early morning, at a time when plasma cortisol (which is associated with Th2-type cytokine production) is lowest and MLT is highest.

Diurnal rhythmicity in healthy humans between cellular (Th1) or humoral (Th2) immune responses is related to immunomodulatory actions of cortisol and melatonin. The blood plasma or serum interferon gamma (IFN-γ) to interleukin-10 (IL-10) ratio peaks during early morning and is inversely correlated with plasma cortisol and positively with plasma melatonin. Taking the autoimmune condition RA as illustrative of such processes, accordingly, the intensity of RA-related pain varies in a diurnal manner: it is greatest early in the day, soon after waking, compared to afternoon or evening. Low plasma cortisol in untreated RA patients and "relative adrenal insufficiency" in the context of sustained inflammatory process allows Th1 cytokines to be produced in higher amounts during early morning hours. Likewise, deficient up-regulation of the anti-inflammatory IL-10 and Transforming Growth Factor-beta (TGF-β) cytokines allows IL-1, IL-6, IFN-γ and other Th1 cytokines to be transiently produced in higher amounts.

Until the recent advent of inexpensive, miniature, wearable, high-frequency, data-logging sensors possessing data communication capabilities and/or persistent machine-readable data storage, such as RF beacons 180 having temperature sensors and flash memory, it was not practical to monitor how such cytokine and neuroendocrine transients are manifested in short time-frame fluctuations in body temperature or other organism-level properties of healthy persons or of persons having autoimmune or other health conditions. With capability to acquire such high-frequency thermometry data for body temperature, this data can be processed by and interpreted according to the novel system and method embodiments described herein to provide useful, actionable applications including personalizing or tailoring the prescription of medications to patients specific conditions and/or invoking other actions, such as notifying a caregiver, modifying care or treatment of a patient, scheduling consultations, providing recommendations, or other actions described herein.

Accordingly, at step 310 temperature information for a patient is received. Some embodiments of step 310 include measuring or recording temperature information of a target patient. The temperature information may comprise nocturnal or ultradian core or axillary temperature information, and may be received or derived from periodic RF beacon transmissions emitted by a temperature sensor-enabled beacon device, such as an RF beacon 180 (described in FIG. 1B), which may be worn by the patient. In some embodiments, at least 4 hours' measurements are acquired in each nighttime sleep episode, comprising the bathyphase of the patient's diurnal temperature cycle. In some embodiments, temperatures are measured at a high sampling rate, such as at least one measurement per minute.

In some embodiments, the temperature information may be received by a mobile device 120 (or a wireless-communications enabled RF beacon reader device), by computing system 130, or may be further communicated to computing system 130, if received by mobile device 120. In this way, the operations performed in method 300 may be carried out on mobile device 120, computer system 130, server 140, other computing devices or components (e.g., monitor 141 or RF beacon 180) described herein, or may be distributed across two or more of these systems.

In some embodiments, temperature information may be determined by an RF beacon 180, which may communicate a reference pointer to mobile device 120 (or a wireless-communications enabled RF beacon reader device). In an embodiment, the reference pointer is an address, such as a URL, physical address, logical address, or mapping to a location in information store 132 that stores temperature information for the patient and may also store additional information items, which may be stored in a set of related information items. In an embodiment, a reference pointer is a set of pointers or addresses to all of the individual pieces of information items in the set. In an embodiment, a reference pointer is a code that is associated with an identifier, such as a physical address, or logical address, or table of addresses that identify the set of related information items. For example, in an embodiment, a table or database may be associated with the reference pointer (such as a code or identification number), thereby mapping the reference pointer to the set of information items. One advantage of having a reference pointer as a code and not an actual physical or logical address is that the code can always be the same length. Additionally, the code might be rendered meaningless without the associated identifier; thus, security advantages are provided because the reference-pointer code can be communicated without identifying any information about the set of information items that are associated with the reference pointer. Thus, for example in one embodiment a pseudorandom code can be generated, using computing system 130, and used as reference pointer by associating it with a set of information items including the temperature information. Moreover, the association between the code and the set of information items is made secure so that only a user with authorized credentials can access information in the set of information items. An unauthorized user might not be permitted to see or detect the association, let alone the set of information items.

Accordingly, some embodiments of step 310 include communicating a reference pointer to a mobile device 120 or wirelessly enabled RB beacon reader device. In one embodiment, the reference pointer is sent via SMS text message or e-mail to the mobile device. In one embodiment, the reference pointer is communicated over Bluetooth, Wi-Fi, or other wireless-communication technologies. For example, as described herein, the reference pointer may be communicated via a wireless-communication beacon such as RF beacon 180. In an embodiment, the reference pointer is encoded in a communication emitted from RF beacon 180. For instance, the reference pointer may be communicated over Bluetooth Low Energy (BLE, such as Bluetooth 4.0) or other short-range wireless-communication technologies, in an embodiment. In one embodiment, the reference pointer is communicated to the mobile device as an update within an app. For example, an app running on the mobile device might include functionality as described above for identifying RF beacon emissions and receiving the reference pointer.

Some embodiments of step 310 further include receiving a request by the mobile device 120 (or RF beacon reader device) for at least a portion of information (such as temperature information) from the set of information associated with the reference pointer. In one embodiment, mobile device 120, having received the reference pointer, now requests information pointed to by the reference pointer. The request may be received by server 140, subscription service 190, or a server operating on computing system 130, in an embodiment. For example, in one embodiment, if a clinician-user has subscribed to rheumatoid arthritis information about a particular patient, the clinician-user's mobile device 120 (having received the reference pointer, which points to information from the set of rheumatoid arthritis-related information) now communicates a request for at least a portion of that information, such as one or more temperature measurements, that is associated with the reference pointer. In one embodiment, mobile device 120 communicates the reference pointer, or information associated with the reference pointer such as a portion of the reference pointer code, to server 140 or subscription service 190.

In one embodiment, mobile device 120 (or an RF beacon reader device) may also communicate credentials or authorization information. In some embodiments, credentials or authorization information includes user credentials, subscription credentials, or both. In one embodiment, user credentials identify the user, which can be used to determine which information or which types of information a user is permitted to access. In one embodiment, user credentials do not identify the user, but specify the information or types of information that a user is permitted to access. Subscription credentials specify information about the user's subscription, which in one embodiment, can be discretized to a per-patient or per-information item level. In one embodiment, subscription credentials include authorization information from the third party for which the information is concerning. In one embodiment, subscription credentials specify how long a particular information item or set or subset of information items, can be accessed. For example, if a user is authorized to access data for a patient only for a specified period of time, then after the credential expires, the user will no longer be permitted to access updated information for that patient. In one embodiment, a user may only desire to know about a third-party patient for a given amount of time. In the proceeding embodiments, the user's subscription to a set of information items or a particular information item may expire after a period of time. In one embodiment, the mobile device will no longer request information after the subscription has expired. In one embodiment, the mobile device will display an indication to the user that the user's credential has expired or that the user is not permitted to access the information requested.

In some embodiments, computer system 130 or server 140 may include a service such as access control permissions services 223 for authenticating a user as a medical provider authorized to receive the medical data based on a location of the user near at least one beacon located in association with a patient for which the medical data is provided. The patient and beacon can be located in a room within a hospital, medical facility, medical clinic, etc. The mobile device 120 (or RF beacon reader device) may further enable the medical provider to obtain the relevant information about the patient, and related information including receiving treatment checklists, obtain treatment guidance, recording a medical procedure as video via a camera (e.g., video camera) integrated with the mobile device 120 and make medical annotations while treating the patient. The annotations and video can be securely stored in the patient's EHR 160 or in a server (e.g., server 140 or computer system 130) as a medical record in association with the patient and made available for subsequent retrieval by authorized medical providers. Checklists and health guidance can also be obtained from the server. Note that in an embodiment, a step or logical operation can be provided for authenticating an identity of the healthcare provider prior to authorizing access to the healthcare records. In an embodiment, authentication for access may comprise: at least one of acquiring a biometric; and acquiring entry of a passcode from the healthcare provider; and an RFID tag and/or NFC-enabled credentialed smartcard or worn bracelet that is challenged throughout a healthcare facility (e.g., upon entry into a patient's room, wherein a patient awaits treatment).

In one embodiment, the healthcare provider can revoke or grant credentials at any time. For example, in one embodiment, the healthcare provider maintains a database, which takes the form of a relational database of credential information associated with users, patients, or concepts. Using this database, the healthcare provider can alter credentials associated with a patient, user, or concept, at any time. Thus, the information that a user is permitted to access can be controlled dynamically by the healthcare provider. By way of example, if the healthcare provider determined that a particular user is no longer permitted to have access to information about a particular patient, then the credential information in the database that is associated with that user and that patient would be set so as to prevent access to the patient information, thereby effectively revoking credentials, in one embodiment.

In one embodiment, a third party, such as a patient, is permitted to provide input for determining credentials. For example, a patient might set access-permission levels; in one embodiment, the patient might do this by logging on to a secure website maintained by the healthcare provider. In one embodiment, the third party may identify particular information items for which they desire to block access. In one embodiment, the third party might consent, or provide permission, to allowing information items to be made accessible to a user, such as their doctor, using the technologies described herein. In one embodiment, the third party provides the consent by logging on to the secure website. In embodiments such as these, the third party is provided control over what information is made accessible, to whom it is accessible, and for how long it is accessible.

In some embodiments, a user may only desire to know about a third-party patient (or similar target) when the user is in spatial proximity to the third party patient. In the proceeding embodiments, the user's subscription to a set of information items or a particular information item may expire once the user is no longer in spatial proximity, such as when the user's mobile device 120 no longer detects communication from an RF beacon 180. In one embodiment, the mobile device will no longer request information after the subscription has expired.

Some embodiments described herein may be configured to monitor beacons and respond, such as by communicating a callback when a user mobile device is sufficiently close to one or more beacons and, in some instances, when corresponding proximity rules are triggered. As described above, beacons may emit or broadcast information continuously, periodically or in response to a ping or hail from a detecting device. Certain hardware beacons, such as iBeacons are Bluetooth Low Energy devices which keep emitting their identity at a predefined frequency (e.g., every 500 milliseconds), this broadcasting is also known as advertising interval. These signals are emitted at a fixed transmission power which is usually measured in dBm (dB-milliWatt). Typical values are −4 dBm, −8 dBm, −16 dBm. These signals can be detected by mobile device at distances up to approximately 70 meters.

In a typical deployment scenario where multiple beacons might be deployed as close as 50 centimeters from each other, a mobile device would receive signals from more than one beacon at a time. All the beacons may be configured to have the same UUID which is common to the organization. However, each one may be configured to have a different identity as defined by two other numeric codes (Major and Minor) plus, optionally, additional tags. UUID: 16-byte number typically common across an organization, e.g., Major: 2-byte number (0 to 65,535), Minor: 2-byte number (0 to 65,535). In the embodiments described herein that use tags: a list or vector of 4-byte numbers (0 to 4,294,967,295) may be used with each vector element denoting a concept or attribute or property or an entity with which the beacon-bearer has a relationship. In these embodiments, the combination of UUID, Major, and Minor may be unique, thereby making each beacon readily identifiable from other beacons.

In some embodiments, each subscription or requested information item has a subscription ID or information item ID that also may be received at step 310. In one embodiment, the ID includes information about the time that the last update for that subscription or information item was received. Alternatively, the received request can include information specifying when a particular update was last received. In some of these embodiments, server 140, subscription service 190, or other software services, routines, or agents operating on computing system 130 may determine the time duration since the last update was received and/or which update was last provided to the mobile device. Accordingly, by receiving information about which updates or subscriptions are on the mobile device, server 140 or subscription service 190 can determine which updated information should be provided to the user. Moreover, in some embodiments, the received information about which updates or subscriptions are on the mobile device is used as criteria for prioritizing (or ranking) information items to be provided to the mobile device. For example, suppose that subscription service 190 received information indicating that the last temperature-related information on a mobile device is from over 1 hour ago, then this information may be used to assign a higher priority (or better ranking) to temperature-related information, thereby increasing the likelihood that temperature-related information will be provided in the next update of information sent to the mobile device.

Further, in some embodiments of step 310 that include receiving a request by the mobile device 120 (or RF beacon reader device) for temperature or other patient information, the request may be accompanied by other information, such as for example, information about the mobile device sending the request such as its location, the mobile service provider (e.g., AT&T, Verizon, or Sprint), the mobile device's signal strength, or the number of subscriptions to which the user is subscribed. In these embodiments, this information may be used as criteria for prioritizing the set of related information items, or may be used to control which information items are communicated to the mobile device, and when those information items are communicated to the mobile device. For example, in situations where the mobile device has diminished signal strength, is roaming, or has a smaller-bandwidth connection such as a 3G connection, it may be advantageous, in some embodiments, to provide fewer information items to the mobile device, or throttle the communication of information items to the mobile device. Thus, only higher priority or ranked information items, or information items determined to be critical or urgent, would be communicated to the mobile device, in these embodiments. Similarly, in situations where the mobile device is in spatial proximity to multiple RF beacons 180, information items corresponding to those patients or targets that are nearer to the user may be prioritized or ranked higher. Nearness may be determined, by way of example and not limitation, based on signal strength of the RF beacon and/or by comparing the location of the mobile device 120 (or RF beacon reader device) and a known location of the RF beacon 180 (such as a particular patient bed or hospital floor). In this way, a user moving through a hospital (or any setting with multiple RF beacons 180) may only see information for those targets closest to the clinician-user.

In some embodiments, the requested information item(s) such as the temperature information received in step 310 is provided to a mobile device 120 (or RF beacon reader device) using either "push" or "pull" technologies. For example, in one embodiment, the subset is provided as a "push" of information by way of a data connection. In another embodiment, the mobile device "pulls" the subset of information items. In one embodiment, the mobile device receives a notification that updated information is available, and an app running on the mobile device initiates a communication session to receive the subset of information items. It is further contemplated that in some embodiments communication of this information is done securely so as to minimize the possibility of information theft and comply with HIPPA requirements. For example, the reference pointers or communicated information may be encoded and/or require credentials, as described herein.

In some embodiments, before or after the subset of information items is provided, a user is able to request additional information about a patient, such as by using his or her mobile device 120. For example, in some embodiments, an app (such as application 143, described in FIG. 1B) running on the mobile device may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device. Such feedback may be securely communicated to server 140, in one embodiment.

It should be appreciated that some embodiments described herein benefit a user by providing access to other records associated with a patient. Embodiments may enable health care professionals to access a patient's medical treatment records; however, a primary care physician (PCP) with long-term patient relationship may benefit from having access to a patient's health maintenance records (e.g., records associated with fitness, diet, physical therapy, etc.) as well as educational records, or other records. For example, a patient's school records from K-12 may provide additional insight to a therapist working with the emotional or psychiatric needs of the patient. There may be information (e.g., discipline, grade reports, etc.) that can be helpful in identifying the trigger for a patient's state of mental health. Record form additional training and education may also be considered useful. Similarly, records from employees, military, etc. could offer similar insight and benefits to a treating physician or caregiver.

In some embodiments, a confirmation that the subset of information was delivered to the mobile device, occurs. For example, in one embodiment, mobile device 120 sends an indication of receipt of the subset of information to subscription service 190 or server 140. In one embodiment, this receipt is further used to determine which updates to provide to a particular user's mobile device, based on which updates have already been received, and in one embodiment the receipt is used as criteria for ranking or prioritizing the information items in the set of information items. For example, if a mobile device was unable to receive updates for a period of time, such as 18 hours, then a particular information item, such as a patient's pulse from 17 hours ago, may no longer be included in the subset of information items communicated to the mobile device because it is less significant or useful to the user (i.e., it has dropped in ranking or priority). Whereas, if that particular information item would have been included for an update received 16 hours ago, it would no longer be included in the next update communicated to the mobile device.

As described above, some embodiments may utilize triggering rules and corresponding actions for detecting a beacon and/or receiving specific information from a patient identified form a reference pointer communicated from a beacon. A triggering rule may comprise a combination of multiple conditions, the primary condition being proximity to a beacon. Other conditions may include time spent near the particular beacon or other user attributes configurable via custom attributes as described herein. In one embodiment, an example rule may comprise: IF (the clinician's mobile device 120 running an app 143 to detect an RF beacon 180) has camped onto RF Beacon 180 with Major:231 Minor: 4328 (beacon identification) AND the clinician user has spent more than <30> seconds in the proximity of this beacon AND the clinician user is a provider of care services for the <St. John Depression Group Therapy> group AND the beacon bearer (i.e., the target patient) is <female> AND the beacon bearer has an active diagnosis of <bipolar depression> AND a beacon tag denotes that the beacon bearer is a member of the <St. John Depression Group Therapy> group AND the group has a scheduled meeting <today> AND the date is between the <1st and 31st of January> AND there are simultaneously <two> or more additional Beacons present whose bearers are members of the <St. John Depression Group Therapy> group), THEN (send a callback to the clinician mobile device app 143 with a reference to the Rule name, AND send a callback with a reference pointer to the tagged therapy group AND send information pertaining to the user plus other actions for the identified group as configured by the manager of an administration console).

In some embodiments, rules may have corresponding actions that may be executed. In the example reduction-to-practice described below, five types of actions were configured from the communications service: Text Alert, Webpage, Cards, Webhook and Custom. Text Alert: This is the basic action type, which shows a popup alert on the user mobile device with a text message when the rule is triggered; Webpage: This directs the app by referencing an internet URL and the corresponding ASP or RESTful webpage is opened; Cards: This directs the app to render full-screen content appropriate to the context, configurable from the Admin Console; Webhook: This makes calls to EHR services with given JSON payload; and Custom: This allows one to add fixed JSON payload from the Admin Console. When the rule is triggered, the payload is passed from the communications service to the app, which can parse it and execute other tasks or methods.

Continuing with method 300, at step 320, a temperature time series may be determined from the temperature information received from the RF beacon, which may be received over several weeks or more of nightly sleeping episodes. Examples of time series of temperature information for a patient having Rheumatoid Arthritis and a healthy control patient are illustratively provided in FIGS. 7A and 7B, respectively.

At steps 330 and 340, preprocessing operations maybe performed on the temperature information time series. For example, at step 330 in the example method 300, the silent leaders or trailers of the time series may be trimmed or outlying temperature values (which may represent temperature readings acquired when the RF beacon or temperature sensor was not in contact with a patient's body and thus provided an erroneous temperature reading) may be removed. In some embodiments, as shown in step 340, preprocessing may include de-trending, demeaning, and cleaning the time series (e.g., eliminating outliers, normalizing, or signal conditioning). In some embodiments, preprocessing may include apodizing the temperature time series.

At step 350, a number M of recent temperature time series entries are then extracted to generate a time series of recent temperature measurements. In some embodiments, the length of the time series is at least eight thousand measurements; for example in one example embodiment reduced to practice, the extracted recent temperature time series comprises 8,192 measurements. In some embodiment, a current day or nights temperature information may be appended to the time series of recent temperature measurements.

At step 355, method 300 determines whether a sufficient number of nightly temperature measurements have been acquired or received. If not and if method 300 continues, then method 300 proceeds to step 390 and waits for a time interval before receiving or determining additional temperature information. In some embodiments of step 390, method 300 may wait for the next minute to receive an additional temperature measurement or may wait until the next night when the patient is sleeping and in proximity to an operating temperature-sensor beacon. If at step 355, however, enough nightly temperature measurements have been received, then at step 360 a spectral analysis is performed on the temperature time series. Embodiments of step 360 perform a spectral analysis to determine a spectrum slope (1/F slope) and intercept in frequency passband. In some embodiments, the slope of the temperature power spectrum within a frequency passband is given as approximately $-1/f^a$, in dB/decade of frequency, as a function of logarithmic-scale frequency and logarithmic-scale power (dB), where a is between 1 and 3. In some embodiments, the frequency passband extends from $1.0 \cdot 10^{-2}$ to $5.0 \cdot 10^{-1}$ min$^{-1}$. Some embodiments of step 360 use computation services 126 including the psd module in the R-system, described in FIG. 1B. An example of a computer program routine for performing step 360 (and other steps of method 300) is illustratively provided in FIGS. 4A-4C.

Next at step 370, a comparison of the spectrum analysis results (the spectrum slope or the intercept) versus baseline values is performed. In some embodiments, the baseline values which may be established from a reference patient or population or based on the patient's own previous values. For example, the baseline values may be determined from a spectrum analysis on temperature time series of a healthy control population, such as described in the example embodiment reduced to practice. For instance, the baseline may be derived from patients without having an autoimmune inflammatory condition or from patients who have this condition but who are not experiencing inflammation or a current autoimmune inflammatory event. In some embodiments, of step 370, quantile regression of power spectra is used to determine the difference. In particular, in some embodiments, quantile regression of power spectra may be utilized in step 370 to determine how far the target autoimmune patient deviates from a normal (i.e., baseline) spectrum slope and/or intercept or the spectrum slope and/or intercept determined from the target patient's previous values.

At step 375, based on the comparison if there is a meaningful difference (such as a difference exceeding a threshold), then method 300 proceeds to step 380. But if the difference threshold is not satisfied in step 375, then method 300, if it continues, may proceed to step 390 and wait for a time interval, as described above. In some embodiments, the difference threshold may be predetermined, determined empirically, or based on information about the particular patient (such as the patient's condition), caregiver, a treatment context (e.g., the treatment venue, role of the caregiver, insurer, or other clinical conditions or events associated with the patient). In some embodiments, the difference threshold is five or ten percent tolerance of variance or change.

At step 380, if the difference threshold is exceeded or satisfied, then one or more actions may be carried out automatically or may be recommended, such as, without limitation, intervening in the patient's care; modifying a care program for treating the patient, or other actions as described herein. For example in one embodiment, a patient's treatment plan may be modified by tailoring medication (i.e., more accurately prescribing drugs) to the patient based on their specific condition based on the difference determined in step 370.

At step 385 it may be determined whether to continue method 300 and receive additional temperature information or end the method. If method 300 continues, then method 300 proceeds to step 390, which is described above. Embodiments of method 300 may be repeated continually, periodically, or as needed (or if desired) after a period of time, such as every day/night, weekly, monthly, or the like.

Turning now to FIGS. 5A-5D, illustrative examples of user/clinician interface 142, operating on different types of computer devices, are provided and referenced generally as 501, 502, 503, and 504, respectively. In particular, FIG. 5A depicts an embodiment of a smartphone-based (or mobile device 120 based) application 143 with display showing a graphical user interface 142 comprising an electronic chart. FIG. 5B shows an example embodiment as a display on a wireless-communication-enabled PC computing device, such as computing system 130. In one embodiment, the user interface 142 of FIG. 5B includes a touch screen, and in one embodiment, user interface 142 of 5B includes other input means such as a keyboard, mouse, pad, voice-recognition module, or other means for receiving, from a user, an indication of information items. For example, in one embodiment, a user "checks" a checkbox adjacent to the information items for which he or she is interested in receiving updated information. In another embodiment, a user draws a box or loop around the information items of interest. In another embodiment, the user otherwise selects or provides an indication of information items of interest.

More specifically, in these illustrative examples, 501, 502, and 503 depict a user interface presenting information about a third-party patient named Jane Mary Doe. Each of 501 and 502 has a user interface 142. In these embodiments of user interface 142, a user, such as a clinician or healthcare provider, can select those information items for which the user desires to receive updated information. The clinician-user is thereby subscribing to information related to the selected information items, here "Hypertension" and "Rheumatoid Arthritis," which may enable the clinician-user to receive updates comprising information related to the selection. For instance, the clinician user may receive temperature information, which as described herein and for purposes of the method embodiments disclosed, is related to Rheumatoid Arthritis.

In one embodiment (not shown), the user may draw, with a finger, stylus, mouse, or similar input device, a circle or box around those information items for which the user wishes to subscribe, rather than selecting individual items. Following the receipt or a user's selection of information items, or after an indication of information items is received by a user or agent, an RF beacon 180 corresponding to the patient may be used to communicate the information or to communicate an encoded reference pointer, which points to a set of information items related to the selected information items, in one embodiment.

FIG. 5C illustratively shows an embodiment of mobile device 120. In the embodiment of FIG. 5C, mobile device 120 includes another example of a clinican/user interface 542, which may be a graphical user interface that is presenting a portion of a subset of information from a set of information related to one or more information items to which the user has selected or indicated. Thus, user interface 542 may be embodied as clinician/user interface 142 of FIG. 1B. In one embodiment, the subset of information presented with user interface 542 is facilitated by way of an app (such as application 143 of FIG. 1B) running on mobile device 120. In the example depicted in FIGS. 5A and 5B, a user has subscribed to information relating to hypertension and Rheumatoid Arthritis. User interface 542 depicts an example portion of a subset of information for which this clinician-user might be presented, with these subscriptions. Here, the subset of information includes information about blood pressure and temperature information. In some embodiments, rather than being presented the temperature information, the clinician-user is presented with the results of the comparison performed in method 300, such as an indication of whether the spectrum slope and/or intercept for the patient is meaningfully different from the normal value(s). If so, then the interface 542 of FIG. 5C may present an indication such as an icon or warning indicating that there is a difference (and thus indicating that the patient is experiencing an autoimmune inflammatory event). In some embodiments, interface 542 of FIG. 5C may also present a value indicating the difference, which may be determined as described in step 370 of method 300.

In one embodiment, user interface 542 also presents to the user information about the timeliness of the information item, if available. For example, in the embodiment shown in FIG. 5C, item 580 shows a "Last Update: 7:05 a.m." adjacent to the information item for nocturnal temperature time series. In one embodiment (not shown) user interface 542 presents information about the time that the last update of information was received. In one embodiment, the mobile device maintains access to information about previously received updates, thereby allowing a user to view the changes in levels of a particular information item over time. For example, in the embodiment shown in FIG. 5C, user interface 542 includes a "Time A" button such as Time-delta hotspot 582, adjacent to some of the information items, which when selected, touched, or pressed, enable a user to view the historical information about that information item. In one embodiment, for example, for the information item "Temp" the user may see a chart listing Jane Doe's nocturnal temperature time series for each of the previous updates received by the mobile device. In one embodiment, the previous update levels are presented as a graph (such as depicted in FIG. 7A), thereby enabling the user to more easily and quickly visualize changes in a patient's condition over time.

In some embodiments, user interface 542 contains functionality for receiving input from a user requesting additional information. For example, in the embodiment shown in FIG. 5C, user interface 542 includes show-condition hotspot 584, which when selected, touched, or pressed, directs an app running on the mobile device to provide additional information about the patient's condition to the user via user interface 542. In one embodiment, the additional information includes information that is part of the subset of information already received on mobile device 120. In one embodiment, the additional information is requested from server 140 or subscription service 190. In one embodiment, the additional information includes interpretive information, such as a report or recommendations based on the comparison of the spectral analysis of the patient's temperature information versus the normal values.

In some embodiments, an app (such as application 143 of FIG. 1B) running on the mobile device 120 may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device 120. Such feedback may be securely communicated to server 140, in one embodiment.

Example Actual Reduction to Practice

Example—Single-beacon individual RA care monitoring and management optimization context. In this example. RF beacon 180 comprised a Texas Instruments CC2541F256 BLE chip comprising a 2.4 GHz radio with serpentine antenna on the 28 mm diameter printed circuit board. The CC2541 chip has a 32-bit ARM® Cortex™ MO CPU, 256 KB flash memory, and 8 KB RAM memory. Power to the RF beacon 180 was provided by a CR2032 3-volt lithium cell positioned on the underside of the circuit board. The RF beacon 180 device was enclosed in a two-part white plastic disc assembly whose two halves were press-fit and sealed with a Buna-N O-ring so as to be impervious to 1 m immersion in water, such as shown in FIGS. 6B and 6C. The finished device was provisioned as a token or fob to be worn or carried by target patients. A BLE-enabled clinician user app (e.g., an application 143 operating on a mobile device 120) was implemented on iOS 9.3.5 on an iPhone® smartphone device. In this example, a corresponding patient app was also implemented on iOS 9.3.5 on an iPhone® smartphone device.

Individual patients having rheumatoid arthritis (RA) and receiving care in an employer-sponsored clinic were provided with the disc tokens and downloaded the iOS patient app to their BLE-enabled iPhone® and enabled location services for the app. Each morning upon waking, a patient's beacon uploaded the night's right-axillary temperature time series sampled at 1-min intervals, associated with autoimmune RA management, when triggered by proximity of the user's Bluetooth-enabled smartphone or tabled to the beacon. UUID was generated so as to refer to the employer's occupational health clinic. Individual patients were identified by a reference pointer comprising a Major number code. Age- and gender-matched healthy control subjects were similarly provisioned with RF beacons and mobile apps. Twenty-four consecutive nights' temperature time series were uploaded by members of both groups and deposited in an EHR system 160. Implementation of cleaning, demeaning, detrending, apodizing, power spectrum generation, and spectrum analysis was performed on the data in the EHR system.

Figure 8:
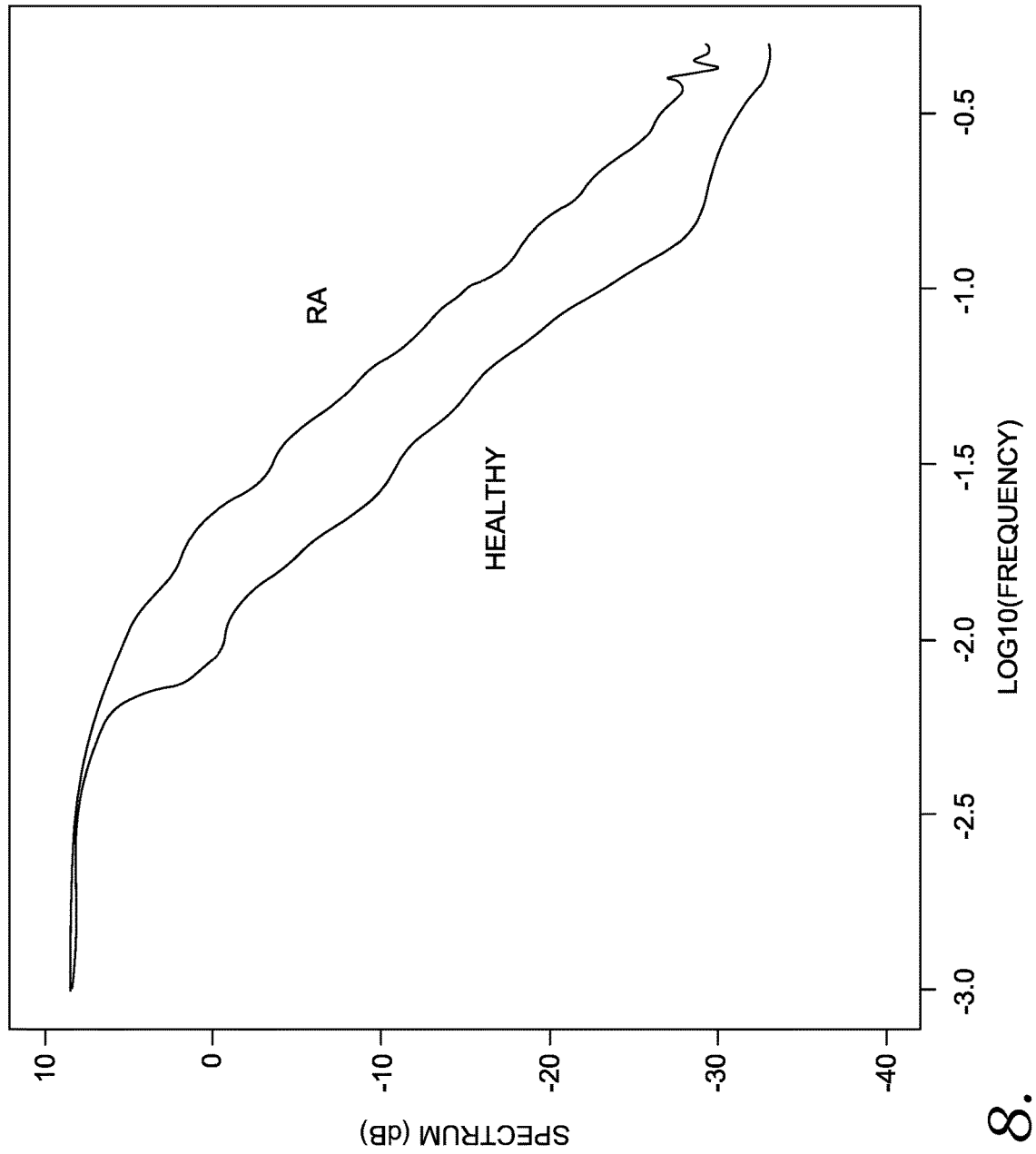
FIG. 8 depicts frequency power spectra of the two example patients described in connection to FIGS. 7A and 7B, determined in accordance with embodiments of this disclosure.

FIG. 8 depicts a comparison of the spectral analyses of the RA patients versus the healthy control. With reference to FIG. 8, among the RA patients studied for the reduction-to-practice, the slope of the power spectrum roll-off was not statistically different from the slope of the power spectrum of the matched healthy control subjects. However, the intercepts of the spectra were significantly different and statistically correlated with active RA symptom severity. The RA spectra were right-shifted and exhibited greater power spectral density at higher frequencies, compared to the spectra of healthy control subjects.

It is notable that older subjects tend to have mean central body temperatures lower than 37° C. Relatively few even achieve this temperature. Among nursing home residents, for example, the oldest tend to exhibit the coolest temperatures and may fail to demonstrate a diurnal rise in body temperature. Similarly, axillary and tympanic temperatures tend also to be slightly lower in elderly persons, compared to younger individuals.

Some therapeutics that are utilized in inflammatory conditions—medications such as aspirin or other non-steroidal anti-inflammatory drugs (NSAIDs), whose anti-inflammatory and analgesic properties result in their usage in autoimmune conditions, such as rheumatoid arthritis treatment—are also antipyretics and tend to affect body temperature regulation as measured in the context of the practice of the present technology. Notwithstanding the antipyretic effects of such concomitant medications, we find that the frequency power spectrum of such patients continues to be right-shifted compared to normal, with abnormally high energy in higher-frequency bands. The temperature time series frequency spectrum is not normalized by administration of antipyretics. Normalization of the temperature time series frequency power spectrum is achieved only when the inflammatory process in the autoimmune disease is substantially interdicted, as happens with efficacious DMARD therapy (such as corticosteroids and methotrexate), often involving an anti-TNF-alpha agent (such as etanercept or infliximab), an anti-IL-6R agent (such as tocilizumab), and/or an anti-IL-1 agent (such as anakinra).

Many different arrangements of the various components depicted, as well as components not shown, are possible without departing from the spirit and scope of the present technology. Embodiments of the present technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the present technology. Some example embodiments include Embodiment 1: A system for providing decision support for a target patient having an autoimmune inflammatory condition, comprising: an RF beacon configured to communicate wirelessly information including temperature information associated with the target patient; a computer device configured to detect an RF beacon and receive the temperature information; one or more processors; and computer storage memory having computer-executable instructions stored thereon which, when executed by the one or more processors, implement a method comprising: receiving by the computer device temperature information communicated from the RF beacon; determining a time series from the received temperature information; performing a spectral analysis on the temperature time series to determine at least one or a spectrum slope and an intercept in a frequency passband; comparing at least one of the determined spectrum slope and an intercept to a baseline; and based on the comparison, invoking one or more actions for the target patient.

Embodiment 2: Embodiment 1, wherein the temperature information is determined at a sampling rate of approximately one temperature measurement per minute.

Embodiment 3: Any of Embodiments 1-2, wherein the baseline comprises a baseline spectrum slope value or a baseline intercept value.

Embodiment 4: Any of Embodiments 1-3, wherein the baseline is determined based on temperature information from one or more patients that does not suffer from an autoimmune inflammatory condition.

Embodiment 5: Any of Embodiments 1-4, wherein the baseline is determined based on an average values of the spectrum slope and intercept for the patient.

Embodiment 6: Any of Embodiments 1-5, wherein the comparison is performed using quantile regression of the determined power spectra.

Embodiment 7: Any of Embodiments 1-6, wherein the one or more actions comprise providing a recommended medication and dosage to be prescribed the patient.

Embodiment 8: Any of Embodiments 1-7, wherein the time series comprises at least eight thousand temperature measurements taken over a time frame of at least 21 days.

Embodiment 9: One or more computer hardware devices having computer-executable instructions embodied thereon that, when executed, facilitate a method of providing clinical decision support, the method comprising: receiving, from a user device, an indication of one or more information items associated with a patient of a user of the user device that are of ongoing relevance to the user in making clinical decisions with respect to the patient's autoimmune condition, where at least one of said items is the patient's high-frequency nocturnal body temperature time series; based on the received indication, determining a set of information items related to the one or more indicated information items; associating a patient with a designated beacon device implementing a short-range RF protocol such as Bluetooth Low Energy (BLE) for proximity-based communications; generating a reference pointer associated with the determined set of related information items; communicating the reference pointer from said beacon device to the user mobile device to enable the user to receive updates to the set of related information items on a mobile device associated with the user via the reference pointer, wherein the mobile device is independent of the user device; receiving from the mobile device a request for information from the set of information items identified by the reference pointer; providing, to the mobile device, information from a subset of the determined set of related information items; registering a wearable BLE temperature sensor-enabled beacon to a patient; affixing said beacon to a region of the patient's body prior to the patient's retiring for sleep at night; maintaining thermal skin contact of said beacon throughout the nighttime sleep interval; measuring the patient's body temperature via said sensor-bearing beacon at frequent fixed-period intervals, preferably once per minute or more, during nighttime sleep; removing said beacon from the patient's body each morning upon waking; ranging said beacon in proximity to a BLE-equipped mobile device periodically, to effect uploading of accrued body temperature time series to a nearby Bluetooth device and thence transmitting said time series information to an electronic health record (EHR) system via web or cellular telephony or other means; repeating the cycle of affixing-removing the beacon to the patient's body on a nightly basis for a plurality of nights comprising at least 21 nights of high-frequency temperature data; trimming, cleaning, demeaning, detrending, and apodizing each said night's temperature time series; concatenating said plurality of individual nights' temperature time series data to form one unified time series comprising at least 8,192 temperature measurements in all; determining a power spectrum of said concatenated temperature time series by Fast Fourier Transform or Wavelet Transform or other means; determining the slope and intercept of a log-log representation of said power spectrum; determining whether said spectrum slope and intercept differ from normal values or differ from the patient's own previous values, if any; and electronically presenting said spectrum-analytic interpretive information pertaining to the patient to an authorized clinician or caregiver user.

Embodiment 10: Embodiment 9, wherein the providing, to the mobile device, information from a subset of the determined set of related information items is in response to determining that at least one of the related information items has been updated.

Embodiment 11: Any of Embodiments 9-10, wherein determining a set of information items further includes determining a priority of the information items based on one or more criteria.

Embodiment 12: Any of Embodiments 9-11, wherein the criteria for determining a priority are based on at least one of: user preferences, user history information, staleness of the information item, condition of the patient, information items in the set of information items, the user device, or a significance-value associated with an information item.

Embodiment 13: Any of Embodiments 9-12, wherein the subset of information items includes a portion of items, from the set of information items, having a higher priority than another portion of items, from the set of information items, having a lower priority.

Embodiment 14: Any of Embodiments 9-13, wherein the reference pointer is encoded within a BLE beacon as a UUID, Major number and Minor number codes, and, optionally, associated tag attribute codes stored within the beacon device's flash memory.

Embodiment 15: Any of Embodiments 9-14, wherein the method further comprises receiving from the user device credentials-information.

Embodiment 16: Any of Embodiments 9-15, wherein the credentials-information includes at least subscription credentials, associated with a duration that the set of information items is accessible to the user.

Embodiment 17: Any of Embodiments 9-16, wherein the reference pointer comprises an address corresponding to the set of information items or an index code that identifies or categorizes the set of autoimmune-related information items as structured discrete data elements, either of which is usable for identifying the set of information items.

Embodiment 18: Any of Embodiments 9-17, wherein the reference pointer is set to expire, wherein expiry of the reference pointer acts to revoke access to the set of information items.

Embodiment 19: Any of Embodiments 9-18, further comprising providing to the user device update information for the subset of information items either by automatically pushing the update information to the user device or in response to a pull request from the user device.

Embodiment 20: One or more computer hardware devices having computer-executable instructions embodied thereon that when executed, facilitate a method of providing clinical decision support using a mobile device of a user, the method comprising: receiving, on the mobile device, information indicated by a reference pointer, wherein the reference pointer identifies a set of information items related to a subscribed-to information item associated with a patient of the user, wherein the subscribed-to information item is of ongoing relevance to the user in making clinical decisions with respect to the patient; communicating the information indicated by the reference pointer to a server; receiving on the mobile device a subset of information items from the set of information items related to the subscribed-to information item associated with the patient; and displaying on the mobile device at least a portion of the received subset of information to aid the user in making a clinical decision with respect to the patient.

Embodiment 21: Embodiment 20, wherein the subset of information items is determined, from among the set of information items, based on one or more criteria.

Embodiment 22: Any of Embodiments 20-21, wherein the criteria include: user preferences, user history information, user history information, staleness of the information item, condition of the third person, information items in the set of information items, the user device, or a significance-value associated with an information item.

Embodiment 23: Any of Embodiments 20-22, further comprising communicating credentials-information to the server.

Embodiment 24: Any of Embodiments 20-23, wherein the credentials-information includes subscription credentials, associated with a duration that the set of information items is accessible to the user.

Embodiment 25: A system for providing communications and clinical decision support comprising: a user interface for receiving a user's selection of one or more information items, associated with a patient of the user, that are of ongoing relevance to the user in making clinical decisions with respect to the patient; a computing device for determining a set of information items related to the selected information items and facilitating the generating of a reference pointer that identifies the set of information items; and a server configured for receiving a request from a mobile device for information from the set of information items identified by the reference pointer and providing to the mobile device information from a subset of the set of information items, to aid the user in making a clinical decision with respect to the patient.

Embodiment 26: Embodiment 25, further comprising the mobile device, wherein the mobile device is for receiving the reference pointer and information from a subset of the set of information items and for displaying at least a portion of the subset.

Embodiment 27: Any of Embodiments 25-26, wherein the system is operable to communicate the reference pointer to the mobile device using the server.

Embodiment 28: Any of Embodiments 25-26, wherein the computing device is operable to encode the reference pointer as a composite code, comprising a UUID plus major and minor BLE codes and, optionally, one or more attribute tag codes, and communicate said reference pointer to the mobile device via a short-range RF protocol, such as Bluetooth Low Energy (BLE).

Embodiment 29: Any of Embodiments 25-26, wherein the means for accomplishing said communication and clinical decision support is a BLE-enabled app on the user mobile device.

Embodiment 30: Any of Embodiments 25-26, wherein the app on the user mobile device is implemented as a SMART on FHIR app to facilitate interoperability among different electronic health record systems, insurer or health plan systems, pharmaceutical manufacturer and patient assistance systems, clinical trial data management systems, registry systems, or other health-related information systems, such as public health information systems.

Embodiment 31: Any of Embodiments 9-15, wherein the organization and service are encoded in the UUID, the patient identifier is encrypted in the 16-bit Major number, and one or more related context identifiers are encrypted in the 16-bit Minor number stored on the beacon device.

Embodiment 32: Any of Embodiments 9-15, wherein the organization and service are encoded in the UUID, the patient identifier is encrypted in the 32-bit segmented key comprised of the Major number and Minor number codes stored on the beacon device, and one or more related context identifiers are encrypted on local flash memory on the beacon device.

Embodiment 33: Any of Embodiments 9-15, wherein the organization and service are encoded in the UUID, the patient identifier is encrypted in the 32-bit segmented key comprised of the Major number and Minor number codes stored on the beacon device, and one or more related context identifiers are encrypted on mass storage memory on the EHR system and are retrievable by a suitably authorized mobile app.

Embodiment 34: Any of Embodiments 9-15, wherein the said autoimmune disease may be rheumatoid arthritis, systemic lupus erythematosus, inflammatory bowel disease, psoriasis, multiple sclerosis, celiac disease, Graves' disease, Type 1 diabetes mellitus, or hemophagocytic lymphohistiocytosis (HLH) or its prodrome.

Embodiment 35: Embodiment 9, wherein the sensor of the BLE beacon device is a miniature wireless electronic thermometer, comprising: a temperature measurement means; and a securing means configured to attach the temperature measurement means to a body part, wherein the temperature measurement means is a non-interventional means and allows repeated temperature readings, the temperature measurement means comprising: a temperature sensor; a controller coupled to the temperature sensor and configured to control the temperature sensor to acquire a temperature measurement data; a transmitter coupled to the controller and configured to transmit the temperature measurement data in a wireless manner; and a power supply module configured to provide power to each of the temperature sensor, the controller and the transmitter.

Embodiment 36: Embodiment 35, wherein the securing means is a paper- or elastomer-substrate medical adhesive tape and whose adhesion principal is a hypoallergenic adhesive compound capable of maintaining the beacon in-place for the entirety of a nighttime sleeping episode yet is amenable to convenient detachment of the beacon and adhesive tape upon waking, wherein said detachment can be accomplished without undue pain, discomfort, or injury to the skin or soft tissues.

Embodiment 37: Any of Embodiments 35-36, wherein the transmitter comprises a wireless module and an antenna coupled to the wireless module.

Embodiment 38: Any of Embodiments 35-37, wherein the power supply module is an electrochemical battery, such as a disposable lithium-ion coin cell or lithium polymer rechargeable cell.

Embodiment 39: Any of Embodiments 35-38, wherein the power supply module is a module capable of collecting an ambient energy.

Embodiment 40: Any of Embodiments 35-39, wherein the temperature sensor has a measuring accuracy and precision of ±0.06° C. or better, a temperature-measuring range spanning at least 35° C. to 42° C., and internal temperature stability with measurement drift not greater than ±0.02° C./hr.

Embodiment 41: Any of Embodiments 35-40, further comprising: a receiver configured to read the temperature measurement data in a wireless manner; and an application program installed in the receiver.

Embodiment 42: Any of Embodiments 35-41, wherein the receiver is one selected from the group consisting of a mobile phone, a laptop computer, a tablet computer and a special reader.

Embodiment 43: Any of Embodiments 35-42, wherein the receiver is configured to read the temperature measurement data by means of remote control, and the application program installed in the receiver is configured to analyze the read temperature measurement data and automatically give an alarm if the temperature measurement data is deviated from a preset range, or subject the temperature measurement data to storage, accumulation and further analysis if within the preset range.

Embodiment 44: Any of Embodiments 35-43, wherein the receiver is configured to read the temperature measurement data in a real-time manner, or a temporally random manner or a regular manner.

Embodiment 45: Any of Embodiments 35-44, wherein the thermometer, as a whole, is a disposable article.

Embodiment 46: Any of Embodiments 35-45, wherein the securing means is a disposable article, and the temperature measurement means has a fully enclosed and sterilizable structure.

Embodiment 47: Any of Embodiments 35-46, wherein the wireless mode is Bluetooth Low Energy (BLE).

Embodiment 48: Any of Embodiments 35-47, wherein the temperature sensor module is associated with accelerometer means whereby minute-wise actigraphy determinations as to the sleeping or wakeful activity status of the user may be made.

Embodiment 49: Embodiment 9, wherein the actigraphy determinations are utilized to identify periods of activity and to exclude or censor any said periods of the temperature time record from further analytical steps.

Embodiment 50: Any of Embodiments 9 and 29, wherein the effective thermal time constant of the sensor and its packaging and associated adhesive tape or other means of affixing the device to the user's body is between 0.1 min and 1.0 min and is preferably between 0.2 min and 0.5 min.

Embodiment 51: Any of Embodiments 49-50, wherein the sensor's advertising rate is between 1 sec and 60 sec and is preferably between 2 sec and 10 sec.

Embodiment 52: Any of Embodiments 49-51, wherein the capacity of local memory for storage of date-timestamped serial temperature measurements on the sensor module is sufficient to contain at least 600 minute-wise measurements before storage is reused (overwritten with new values).

Embodiment 53: Any of Embodiments 49-52, wherein the enclosure of the sensor module is relatively impervious against humidity or entry of moisture, to a rating of at least IP57 according to IEC-60529 Table-8 (no dust ingress and no liquid ingress during immersion to a depth of 1 m in water for 30 min).

Embodiment 54: Any of Embodiments 49-53, wherein the RF power of the transmitter of said sensor module is adjustable between 0 dBm and −16 dBm so as to provide reliable reception by BLE-equipped mobile devices at a proximity between 0.1 m and 10 m when the sensor location is axillary and the arm is adducted such that the sensor midule is entirely surrounded by muscle and soft tissue of the body of the user.

Embodiment 55: Any of Embodiments 49-54, wherein the local battery power of the sensor module us conserved by minimizing the duty cycle of RF transmitting and receiving between the sensor and nearby fixed or mobile devices.

Embodiment 56: Any of Embodiments 49-55, wherein the download transfer of stored data of the sensor module to a nearby fixed or mobile device is preferably effected with a frequency not less than weekly but more preferably at least daily following the user's awaking from sleep.

Embodiment 57: Any of Embodiments 49-56, wherein the capacity of local battery power on the sensor module is preferably sufficient for at least 3 days' continuous operation prior to requiring battery recharging or replacement, given the advertising frequency, BLE transmission duty cycle, and RF power level in effect.

Embodiment 58: Any of Embodiments 49-57, wherein temperature measurements by said sensor module are acquired during the user's routine nightly recumbent sleep period, such that a cumulative total of at least 4 hours' measurements are acquired in each nighttime sleep episode, comprising the bathyphase of the subject's diurnal temperature cycle.

Embodiment 59: Any of Embodiments 49-58, wherein temperature measurements during sleep are performed recumbent where the head of the bed is at an angle of 45° or less, the bed being equipped with conventional linens and bed cover or duvet but not with an electric blanket, waterbed heater, infrared heater, or other powered heating devices.

Embodiment 60: Any of Embodiments 49-59, wherein temperature measurements during sleep are performed with the subject clothed in customary light-weight pajamas or nightgown or nightshirt or, optionally, no clothing at all.

Embodiment 61: Any of Embodiments 49-60, wherein temperature measurements during sleep are performed with the subject's head uncovered an exposed to ambient room temperature air between 15° C. and 35° C.

Embodiment 62: Any of Embodiments 49-61, wherein serial nights whose data are concatenated need not be consecutive. Gaps wherein one or several nights' temperature data are missing from the series to be concatenated do not materially affect the slope or intercept of the temperature power spectra of healthy persons nor of persons affected by autoimmune conditions.

Embodiment 63: Any of Embodiments 49-62, wherein the slope of the temperature power spectrum within a frequency passband is approximately $-1/f^\alpha$, in dB/decade of frequency, as a function of logarithmic-scale frequency and logarithmic-scale power (dB), where a is between 1 and 3.

Embodiment 64: Any of Embodiments 49-63, wherein the frequency passband extends preferably from $1.0 \cdot 10^{-2}$ min$^{-1}$ to $5.0 \cdot 10^{-1}$ min$^{-1}$.

It will be understood that certain features and subcombinations are of utility and may be employed without reference to other features and subcombinations and are contemplated within the scope of the claims. Not all steps listed in the various figures need be carried out in the specific order described. Accordingly, the scope of the technology is intended to be limited only by the following claims.

What is claimed is:

1. A system for providing decision support for an autoimmune inflammatory condition, comprising:
    a temperature sensor;
    a monitoring device;
    at least one processor; and
    computer storage memory having computer-executable instructions stored thereon which, when executed by the at least one processor, perform operations comprising:
        authenticating a user as an authorized medical user based on a proximity of the temperature sensor to the monitoring device;
        receiving temperature information, the temperature information comprising a plurality of temperature measurements;
        determining a time series from the received temperature information;
        performing a spectral analysis on at least a portion of the time series to determine at least one of a spectrum slope and an intercept in a frequency passband;
        comparing at least one of the spectrum slope to a baseline spectrum slope value and the intercept to a baseline intercept value; and
        based on the comparison, automatically initiating one or more actions for the autoimmune inflammatory condition.

2. The system of claim 1, the operations further comprising:
    extracting from the time series a set of temperature measurements that includes a number of most recent temperature measurement of the plurality of temperature measurements; and
    appending a current temperature measurement to the extracted set of temperature measurements, wherein the portion of the time series that the spectral analysis is performed on includes the extracted set of temperature measurements and the current temperature measurement.

3. The system of claim 1, the operations further comprising determining the baseline spectrum slope value and the baseline intercept value from at least one of:
    a historical set of temperature information for an individual associated with the temperature sensor; and
    a population not having the autoimmune inflammatory condition.

4. The system of claim 1, further comprising:
    the temperature sensor wherein the temperature sensor comprises a wearable temperature sensor having a radio frequency (RF) beacon for wirelessly communicating temperature information collected from the temperature sensor.

5. The system of claim 4, wherein a wearable temperature sensor's proximity to the monitoring device is detected using periodic RF transmissions emitted by the temperature sensor.

6. The system of claim 1, wherein a clinical status of a patient is monitored continually in an ambulatory setting.

7. The system of claim 1, wherein the one or more actions comprises at least one of: adjusting a medication regimen for the autoimmune inflammatory condition, modifying a care program for treating the autoimmune inflammatory condition, automatically scheduling interventions or consultations with specialist caregivers, and generating a notification.

8. The system of claim 1, wherein the portion of the time series that the spectral analysis is performed on comprises at least 8,000 temperature measurements, wherein the at least 8,000 temperature measurements are determined over a time frame of at least 21 days.

9. One or more non-transitory computer storage media having computer-executable instructions stored thereon that, when executed by at least one processor, facilitate a method of providing clinical decision support for an autoimmune inflammatory condition, the method comprising:
    receiving temperature information from a temperature sensor, the temperature information comprising a plurality of temperature measurements;
    authenticating a user as an authorized medical user based on a proximity of the temperature sensor to a monitoring device;
    determining a time series from the received temperature information;
    performing a spectral analysis on at least a portion of the time series to determine at least one of a spectrum slope and an intercept in a frequency passband;
    comparing at least one of the spectrum slope to a baseline spectrum slope value and the intercept to a baseline intercept value; and
    based on the comparison, initiating one or more actions for the autoimmune inflammatory condition, the one or more action including adjusting a medication regimen for the autoimmune inflammatory condition, modifying a care program for treating the autoimmune inflammatory condition, automatically scheduling interventions or consultations with specialist caregivers, and generating a notification.

10. The media of claim 9, wherein the temperature information is received from the monitoring device in communication with a radio frequency (RF) beacon of the temperature sensor, a temperature sensor's proximity to the monitoring device is detected using periodic RF transmissions emitted by the temperature sensor.

11. The media of claim 9, wherein the spectral analysis is performed using at least one of Fast Fourier Transform and Wavelet Transform.

12. The media of claim 9, further comprising:
extracting from the time series a set of temperature measurements that includes a number of most recent temperature measurement of the plurality of temperature measurements; and
appending a current temperature measurement to the extracted set of temperature measurements, wherein the portion of the time series that the spectral analysis is performed on includes the extracted set of temperature measurements and the current temperature measurement.

13. The media of claim 9, wherein the baseline spectrum slope value and the baseline intercept value are determined from at least one of:
a historical set of temperature information for an individual associated with the temperature sensor; and
a population not having the autoimmune inflammatory condition.

14. The media of claim 9, wherein the comparison is performed using quantile regression of the determined power spectra.

15. The media of claim 9, wherein the portion of the time series that the spectral analysis is performed on comprises at least 8,000 temperature measurements, wherein the at least 8,000 temperature measurements are determined over a time frame of at least 21 days.

16. The media of claim 9, wherein the temperature information is determined at a sampling rate of at least one temperature measurement per minute.

17. A computer-implemented method for providing clinical decision support for an autoimmune inflammatory condition, the method comprising:
receiving from a temperature sensor, at one or more processors, temperature information, the temperature information comprising a plurality of temperature measurements;
authenticating a user as an authorized medical user based on a proximity of the temperature sensor to a monitoring device
determining, at one or more processors, a time series from the received temperature information;
performing, at one or more processors, a spectral analysis on at least a portion of the time series to determine at least one of a spectrum slope and an intercept in a frequency passband;
comparing, at one or more processors, at least one of the spectrum slope to a baseline spectrum slope value and the intercept to a baseline intercept value; and
based on the comparison, adjusting, by one or more processors, a treatment regimen for the autoimmune inflammatory condition.

18. The method of claim 17, wherein the temperature information is determined at a sampling rate of at least one temperature measurement per minute.

19. The method of claim 17, wherein the portion of the time series that the spectral analysis is performed on comprises at least 8,000 temperature measurements, wherein the at least 8,000 temperature measurements are determined over a time frame of at least 21 days.

20. The method of claim 17, wherein the comparison is performed using quantile regression of the determined power spectra.

* * * * *